(12) United States Patent
Matsunaga

(10) Patent No.: US 9,130,233 B2
(45) Date of Patent: Sep. 8, 2015

(54) METAL COMPLEX, MODIFIED COMPOUND THEREOF AND USEFUL COMPOUND THEREOF

(75) Inventor: Tadafumi Matsunaga, Osaka (JP)

(73) Assignee: SUMITOMO CHEMICAL COMPANY, LIMITED, Tokyo (JP)

(*) Notice: Subject to any disclaimer, the term of this patent is extended or adjusted under 35 U.S.C. 154(b) by 122 days.

(21) Appl. No.: 13/823,257

(22) PCT Filed: Sep. 14, 2011

(86) PCT No.: PCT/JP2011/070941
§ 371 (c)(1),
(2), (4) Date: Apr. 18, 2013

(87) PCT Pub. No.: WO2012/036185
PCT Pub. Date: Mar. 22, 2012

(65) Prior Publication Data
US 2013/0210615 A1 Aug. 15, 2013

(30) Foreign Application Priority Data
Sep. 17, 2010 (JP) ................................. 2010-209067

(51) Int. Cl.
| | |
|---|---|
| H01M 4/86 | (2006.01) |
| C07D 471/22 | (2006.01) |
| C07D 519/00 | (2006.01) |
| H01M 4/90 | (2006.01) |
| C07F 15/06 | (2006.01) |
| B01J 31/18 | (2006.01) |
| B01J 31/22 | (2006.01) |
| H01L 51/00 | (2006.01) |

(52) U.S. Cl.
CPC ............ *H01M 4/8652* (2013.01); *B01J 31/183* (2013.01); *B01J 31/2243* (2013.01); *C07D 471/22* (2013.01); *C07D 519/00* (2013.01); *C07F 15/065* (2013.01); *H01M 4/9008* (2013.01); *B01J 2531/0216* (2013.01); *B01J 2531/845* (2013.01); *H01L 51/009* (2013.01); *H01L 51/0083* (2013.01); *Y02E 60/50* (2013.01)

(58) Field of Classification Search
None
See application file for complete search history.

(56) References Cited

U.S. PATENT DOCUMENTS

| | | |
|---|---|---|
| 2009/0062110 A1 | 3/2009 | Koshino et al. |
| 2010/0086823 A1 | 4/2010 | Koshino et al. |
| 2010/0105909 A1 | 4/2010 | Matsunaga et al. |
| 2011/0015059 A1 | 1/2011 | Matsunaga et al. |
| 2012/0021897 A1 | 1/2012 | Iwata et al. |
| 2014/0066290 A1 | 3/2014 | Koshino et al. |

FOREIGN PATENT DOCUMENTS

| | | | |
|---|---|---|---|
| CA | 2710808 | * 7/2009 | ........... C07D 487/22 |
| JP | 2009-173627 A | 8/2009 | |
| WO | 2007/091616 A1 | 8/2007 | |
| WO | 2008/111568 A1 | 9/2008 | |
| WO | 2008/111570 A1 | 9/2008 | |
| WO | 2012/147952 A1 | 11/2012 | |

OTHER PUBLICATIONS

Fung Lam, et al., "Synthesis of Dinucleating Phenanthroline-Based Ligands", Tetrahedron, 55, 1999, pp. 8377-8384.
Christopher J. Chang, et al., "Structural, Spectroscopic, and Reactivity Comparison of Xanthene- and Dibenzofuran-Bridged Cofacial Bisporphyrins", Inorganic Chemistry, 2002, 41, pp. 3102-3109.
International Search Report issued Nov. 22, 2011 in International Application No. PCT/JP2011/070941 with English translation.

* cited by examiner

*Primary Examiner* — Yun Qian
(74) *Attorney, Agent, or Firm* — Sughrue Mion, PLLC

(57) ABSTRACT

Provided is a compound including residues derived from a compound represented by Formula (1) and a divalent aromatic group, wherein the number of the residues is 2 to 4, the number of the divalent aromatic group is 1 to 3, and the sum of the numbers of the residues and the divalent aromatic group is 3 to 5.

(1)

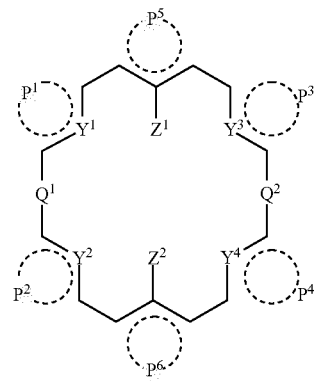

In Formula (1), each of $Y^1$ to $Y^4$ represent a group represented by any of the following Formula (2); in the following Formula (2), $R^\alpha$ represents a hydrogen atom or a hydrocarbyl group; each of $P^1$ to $P^4$ represents an atomic group forming a heterocyclic ring containing $Y^1$ to $Y^4$; $P^5$ and $P^6$ represent an atomic group forming an aromatic ring or a heterocyclic ring; $Q^1$ and $Q^2$ represent a linking group or a direct bond; and $Z^1$ and $Z^2$ represent a hydrogen atom or a group represented by any of the following Formula (3); and in the following Formula (3), $R^\beta$ represents a hydrogen atom or a hydrocarbyl group.

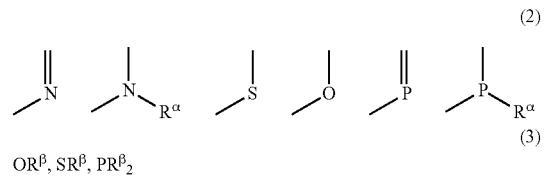

9 Claims, No Drawings

METAL COMPLEX, MODIFIED COMPOUND THEREOF AND USEFUL COMPOUND THEREOF

TECHNICAL FIELD

The present invention relates to a metal complex, a modified compound thereof, and a useful compound thereof.

Priority is claimed on Japanese Patent Application No. 2010-209067, filed Sep. 17, 2010, the content of which is incorporated herein by reference.

A metal complex is known to be useful for an electrode catalyst for a fuel cell. As the electrode catalyst for a fuel cell, an electrode catalyst in which a metal complex which includes of a ligand including one macrocyclic compound or a ligand including residues of one macrocyclic compound and a metal atom is supported on conductive carbon is known (Patent Document 1).

DOCUMENTS OF RELATED ART

Patent Documents

[Patent Document 1] Japanese Unexamined Patent Application, First Publication No. 2009-173627

DISCLOSURE OF INVENTION

Problems to be Solved by the Invention

However, oxygen reduction ability of this electrode catalyst is insufficient.

Accordingly, an object of the present invention is to provide an electrode catalyst having a high degree of oxygen reduction ability, and a metal complex and a compound useful for producing the electrode catalyst.

Means to Solve the Problems

A first embodiment of the present invention is a compound including: residues derived from a compound represented by the following Formula (1); and a divalent aromatic group which may have a substituent, wherein number of the residues is 2 to 4, number of the divalent aromatic group is 1 to 3, and sum of the numbers of the residues and the divalent aromatic group is 3 to 5.

[Chemical Formula 1]

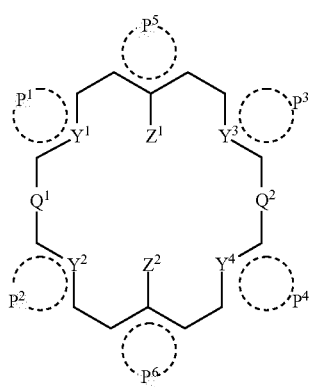

(1)

In Formula (1), each of $Y^1$, $Y^2$, $Y^3$, and $Y^4$ independently represents a group represented by any one of the following formulae:

[Chemical Formula 2]

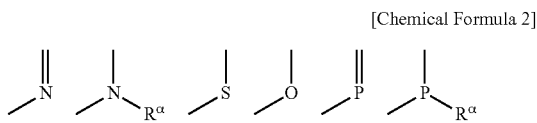

(In the formulae, each $R^\alpha$ independently represents a hydrogen atom or a hydrocarbyl group);

$P^1$ represents an atomic group forming a heterocyclic ring containing $Y^1$; $P^2$ represents an atomic group forming a heterocyclic ring containing $Y^2$; $P^3$ represents an atomic group forming a heterocyclic ring containing $Y^3$; $P^4$ represents an atomic group forming a heterocyclic ring containing $Y^4$; each of $P^5$ and $P^6$ independently represents an atomic group forming an aromatic ring or a heterocyclic ring; each of the heterocyclic rings formed by $P^1$, $P^2$, $P^3$ and $P^4$ and the aromatic ring and the heterocyclic ring formed by $P^5$ and $P^6$ may have a substituent respectively; $P^1$ and $P^2$ may bind to each other to form a ring together with $Q^1$; $P^2$ and $P^6$ may bind to each other to form a ring; $P^6$ and $P^4$ may bind to each other to form a ring; $P^4$ and $P^3$ may bind to each other to form a ring together with $Q^2$; $P^3$ and $P^5$ may bind to each other to form a ring; $P^5$ and $P^1$ may bind to each other to form a ring; each of $Q^1$ and $Q^2$ independently represents a linking group or a direct bond; and each of $Z^1$ and $Z^2$ independently represents a hydrogen atom or a group represented by any one of the following formulae:

   [Chemical Formula 3]

$OR^\beta, SR^\beta, PR^\beta_2$ (In the formulae, each $R^\beta$ independently represents a hydrogen atom or a hydrocarbyl group.).

A second embodiment of the present invention is the compound according to the first embodiment, wherein in the Formula (1), the atomic group represented by $P^5$ binds to $Z^1$ to form a phenol structure, and the atomic group represented by $P^6$ binds to $Z^2$ to form a phenol structure.

A third embodiment of the present invention is the compound according to the first or second embodiment, wherein in the Formula (1), the heterocyclic ring formed by $P^1$, the heterocyclic ring formed by $P^2$, the heterocyclic ring formed by $P^3$, and the heterocyclic ring formed by $P^4$ are aromatic heterocyclic rings.

A fourth embodiment of the present invention is the compound according to the third embodiment, wherein in the Formula (1), the aromatic heterocyclic ring formed by $P^1$, the aromatic heterocyclic ring formed by $P^2$, the aromatic heterocyclic ring formed by $P^3$, and the aromatic heterocyclic ring formed by $P^4$ are nitrogen-containing aromatic heterocyclic rings.

A fifth embodiment of the present invention is a compound according to the first embodiment, wherein the compound represented by the Formula (1) is a compound represented by the following Formula (2).

[Chemical Formula 4]

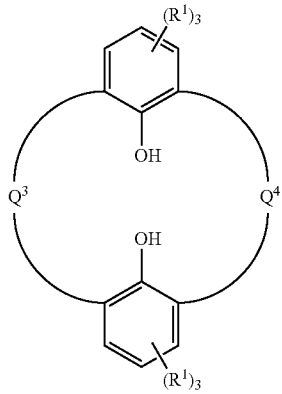

(2)

In Formula (2), $R^1$ represents a hydrogen atom or a monovalent group; a plurality of $R^1$s may be the same as or different from each other; $R^1$s may bind to each other to form a ring; each of $Q^3$ and $Q^4$ independently represents a divalent group represented by any one of the following formulae:

[Chemical Formula 5]

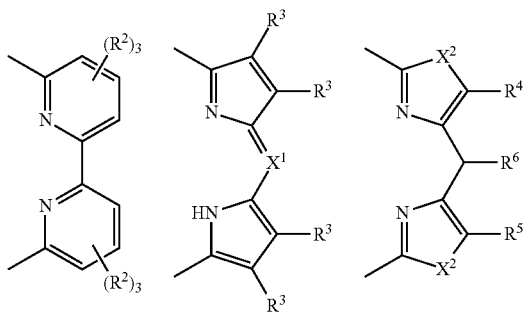

[In the formulae, $R^2$ represents a hydrogen atom or a monovalent group; each of a plurality of $R^2$s may be the same as or different from each other; $R^2$s may bind to each other to form a ring; $X^1$ represents a nitrogen atom or a trivalent group; $R^3$ represents a hydrogen atom or a monovalent group; a plurality of $R^3$s may be the same as or different from each other; $R^3$s may bind to each other to form a ring; $X^2$ represents a group represented by any one of the following formulae:

[Chemical Formula 6]

(In the formulae, R' represents a hydrogen atom or a hydrocarbyl group); a plurality of $X^2$s may be the same as or different from each other; each of $R^4$, $R^5$, and $R^6$ independently represents a hydrogen atom or a monovalent group; $R^4$ and $R^6$ may bind to each other to form a ring; $R^5$ and $R^6$ may bind to each other to form a ring; and $R^4$, $R^5$, and $R^6$ may bind to one another to form a ring.].

A sixth embodiment of the present invention is the compound according to the first embodiment that is represented by the following Formula (3).

[Chemical Formula 7]

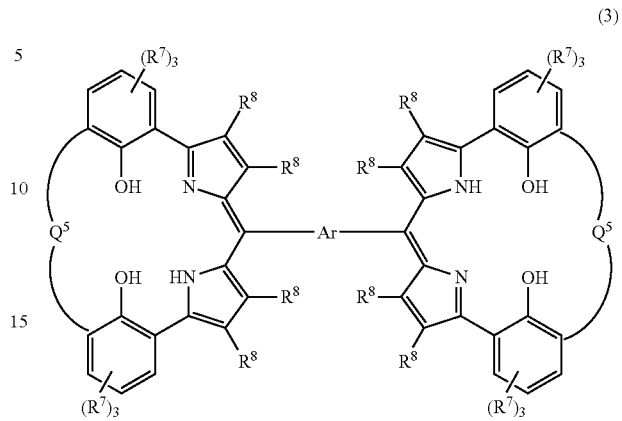

(3)

In Formula (3), each of $R^7$ and $R^8$ independently represents a hydrogen atom or a monovalent group; a plurality of $R^7$s may be the same as or different from each other; $R^7$s may bind to each other to form a ring; a plurality of $R^8$s may be the same as or different from each other; $R^8$s may bind to each other to form a ring; $Q^5$ represents a divalent group represented by any one of the following formulae:

[Chemical Formula 8]

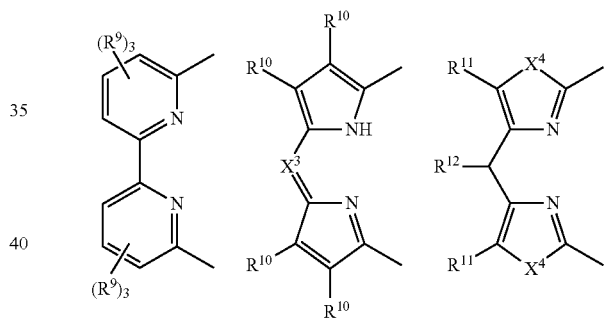

In the formulae, $R^9$ represents a hydrogen atom or a monovalent group; a plurality of $R^9$s may be the same as or different from each other; $R^9$s may bind to each other to form a ring; $X^3$ represents a nitrogen atom or a trivalent group; $R^{10}$ represents a hydrogen atom or a monovalent group; a plurality of RN may be the same as or different from each other; $R^{10}$s may bind to each other to form a ring; $X^4$ represents a group represented by any one of the following formulae:

[Chemical Formula 9]

(In the formulae, R' represents a hydrogen atom or a hydrocarbyl group.); a plurality of $X^4$s may be the same as or different from each other; each of $R^{11}$ and $R^{12}$ independently represents a hydrogen atom or a monovalent group; $R^{11}$ and $R^{12}$ may bind to each other to form a ring.]; a plurality of $Q^5$s may be the same as or different from each other; and Ar represents a divalent aromatic group which may have a substituent.].

A seventh embodiment of the present invention is a metal complex including: a metal atom or a metal ion; and a ligand, wherein the ligand is the compound according to any one of the first to sixth embodiments.

An eighth embodiment of the present invention is the metal complex according to the seventh embodiment, wherein the metal in the metal atom or metal ion is a transition metal belonging to the fourth to sixth periods on the periodic table.

A ninth embodiment of the present invention is the metal complex according to the eighth embodiment, wherein the metal in the metal atom or metal ion is manganese, iron, cobalt, nickel, copper, or platinum.

A tenth embodiment of the present invention is the metal complex according to any one of the seventh to ninth embodiments, wherein the number of the metal atom or metal ion is 1 to 4.

An eleventh embodiment of the present invention is a modified compound which is obtained by heating a mixture including the metal complex according to any of the seventh to tenth embodiments and a carbon support.

A twelfth embodiment of the present invention is the modified compound according to the eleventh embodiment, wherein a temperature of the heating is 600° C. to 1200° C.

A thirteenth embodiment of the present invention is a composition <hereinafter, called a "first composition" in some cases> including: (a) the metal complex according to any one of the seventh to tenth embodiments; and (b) at least one kind of component selected from a group consisting of a carbon support and a polymer.

A fourteenth embodiment of the present invention is a composition <hereinafter, called a "second composition" in some cases> including: (a') the modified compound according to the eleventh or twelfth embodiment; and (b') a polymer.

A fifteenth embodiment of the present invention is a catalyst including: the metal complex according to any one of the seventh to tenth embodiments; the modified compound according to the eleventh or twelfth embodiment; or the composition according to the thirteenth or fourteenth embodiment.

A sixteenth embodiment of the present invention is an electrode catalyst for a fuel cell, including the catalyst according to the fifteenth embodiment.

Effects of the Invention

The electrode catalyst for a fuel cell of the present invention has a high degree of oxygen reduction ability. Moreover, the electrode catalyst for a fuel cell can be easily produced by using the metal complex and the compound of the present invention.

EMBODIMENTS OF THE INVENTION

Hereinafter, the compound of the present invention will be described.

The compound of the present invention is a compound including residues derived from the compound represented by the Formula (1) and a divalent aromatic group which may have a substituent. In this compound, number of the residues is 2 to 4, number of the divalent aromatic group is 1 to 3, and sum of the numbers of the residues and the divalent aromatic group is 3 to 5. The residue derived from the compound represented by Formula (1) is a group including an atomic group obtained by removing a portion or all of hydrogen atoms in the compound represented by Formula (1). The residue derived from the compound represented by Formula (1) is preferably a group having a valency of 1 to 4, and more preferably a monovalent residue.

The compound of the present invention is particularly preferably a compound in which the residues derived from the compound represented by Formula (1) are monovalent residues, the number of the residues is 2, and the number of the divalent aromatic group is 1.

Regarding the compound of the present invention, the mode of binding of the residues derived from the compound represented by Formula (1) to the divalent aromatic group can be schematically described as follows, for example.

C-A-C

C-A-A-C

C-A-C-A-C

C—C-A-C—C

In the formulae, C represents the residue derived from the compound represented by Formula (1); and A represents the divalent aromatic group which may have a substituent.

In the Formula (1), examples of the hydrocarbyl group represented by $R^\alpha$ in $Y^1$, $Y^2$, $Y^3$, and $Y^4$ include linear saturated hydrocarbyl groups having 1 to 50 carbon atoms in total or branched or cyclic saturated hydrocarbyl groups having 3 to 50 carbon atoms in total, such as a methyl group, an ethyl group, a propyl group, an isopropyl group, a cyclopropyl group, an n-butyl group, an isobutyl group, a tert-butyl group, a pentyl group, a cyclopentyl group, a hexyl group, a cyclohexyl group, a norbornyl group, a nonyl group, a cyclononyl group, a decyl group, a 3,7-dimethyloctyl group, an adamantyl group, a dodecyl group, a cyclododecyl group, a pentadecyl group, an octadecyl group, and a docosyl group. Among these, linear saturated hydrocarbyl groups having 1 to 8 carbon atoms in total or branched or cyclic saturated hydrocarbyl groups having 3 to 8 carbon atoms in total are preferable.

In the Formula (1), it is preferable that each of $P^1$, $P^2$, $P^3$, and $P^4$ independently represent an atomic group that is necessary for forming a heterocyclic ring by binding to two adjacent carbon atoms in each of $Y^1$, $Y^2$, $Y^3$, and $Y^4$. Moreover, the "two adjacent carbon atoms" do not include the carbon atoms that can be contained in $R^\alpha$.

In the Formula (1), examples of the heterocyclic ring formed by $P^1$, $P^2$, $P^3$, and $P^4$ include a pyrrolidine ring, a piperidine ring, a morpholine ring, a piperazine ring, a tetrahydrofuran ring, a phosphole ring, a phosphabenzene ring, a pyridine ring, a pyrazine ring, a pyrimidine ring, a pyrrole ring, an N-alkylpyrrole ring, a furan ring, a thiophene ring, a thiazole ring, an imidazole ring, an oxazole ring, a benzimidazole ring, a benzofuran ring, a benzothiophene ring, an isoquinoline ring, and a quinazoline ring. Among these, a pyridine ring, a pyrazine ring, a pyrimidine ring, a pyridazine ring, a pyrrole ring, a furan ring, a thiophene ring, an N-alkylpyrrole ring, and an imidazole ring are preferable; and a pyridine ring, a pyrrole ring, and an imidazole ring are more preferable. In addition, the heterocyclic ring formed by $P^1$, $P^2$, $P^3$, and $P^4$ is preferably an aromatic heterocyclic ring, and more preferably a nitrogen-containing aromatic heterocyclic ring.

In the Formula (1), each of $P^5$ and $P^6$ independently represents an atomic group that is necessary for forming an aromatic ring or a heterocyclic ring.

In the Formula (1), the heterocyclic ring formed by $P^5$ and $P^6$ is the same as the heterocyclic ring that can be formed by $P^1$, $P^2$, $P^3$, and $P^4$.

In the Formula (1), examples of the aromatic ring formed by $P^5$ and $P^6$ include a benzene ring, a naphthalene ring, and an antharcene ring, and among these, a benzene ring is preferable.

In the Formula (1), examples of the direct bond represented by $Q^1$ and $Q^2$ include a single bond and a double bond, and among these, a single bond is preferable.

In the Formula (1), examples of the linking group represented by $Q^1$ and $Q^2$ include divalent groups and trivalent groups. Among these, groups represented by the following Formulae (1-a) to (1-g) are preferable, groups represented by the following Formulae (1-a) to (1-d) are more preferable, and groups represented by the following Formula (1-a) or (1-b) are even more preferable.

[Chemical Formula 10]

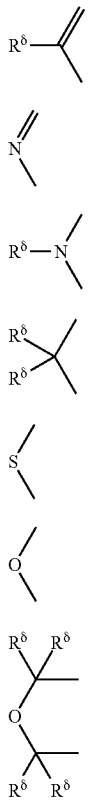

(1-a)

(1-b)

(1-c)

(1-d)

(1-e)

(1-f)

(1-g)

In the formulae, $R^\delta$ represents a hydrogen atom or a monovalent group; and when there are a plurality of $R^\delta$s, these may be the same as or different from each other.

Herein, examples of the monovalent group represented by $R^\delta$ include a hydrocarbyl group which may have a substituent and a monovalent aromatic group which may have a substituent.

The hydrocarbyl group is the same group as the hydrocarbyl group represented by $R^\alpha$.

Examples of the monovalent aromatic group include a phenyl group, a 4-methylphenyl group, a 2,6-dimethylphenyl group, a 1-naphthyl group, a 2-naphthyl group, and a 9-anthryl group.

Examples of the substituent of the hydrocarbyl group and the monovalent aromatic group include a methyl group, an ethyl group, a tert-butyl group, a phenyl group, a naphthyl group, a 1,9-anthryl group, a pyridyl group, and a 1,10-phenanthryl group.

In the Formula (1), when $P^1$ and $P^2$ bind to each other to form a ring together with $Q^1$, or when $P^4$ and $P^3$ bind to each other to form a ring together with $Q^2$, the compound represented by the Formula (1) has, for example, structures represented by the following Formulae (2-a) to (2-o), preferably has structures represented by the following Formulae (2-a) and (2-j) to (2-o), and more preferably has a structure represented by the following Formula (2-a).

[Chemical Formula 11]

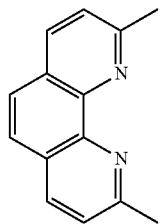

(2-a)

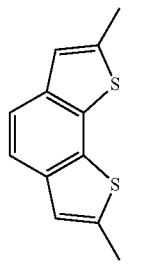

(2-b)

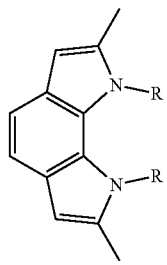

(2-c)

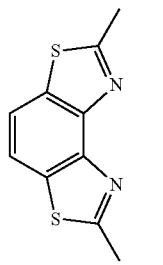

(2-d)

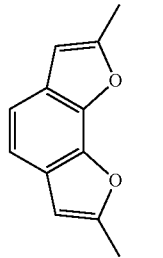

(2-e)

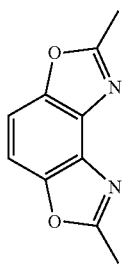
(2-f)

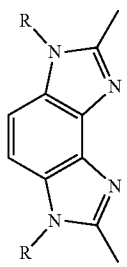
(2-g)

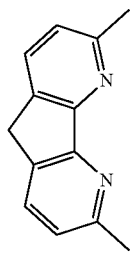
(2-h)

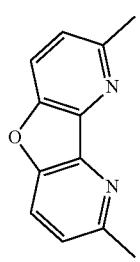
(2-i)

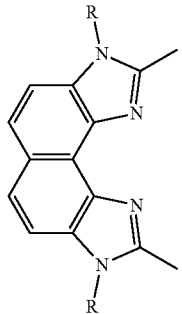
(2-j)

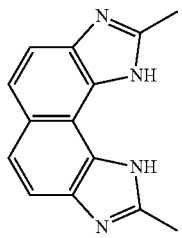
(2-k)

(2-l)

(2-m)

(2-n)

(2-o)

In the formulae, R represents a hydrogen atom or a hydrocarbyl group having 1 to 30 carbon atoms; and two Rs may be the same as or different from each other.

Herein, examples of the hydrocarbyl group which is represented by R and has 1 to 30 carbon atoms include the same groups as the hydrocarbyl group represented by $R^\alpha$, and among these, a hydrocarbyl group having 1 to 8 carbon atoms is preferable.

The heterocyclic ring formed by $P^1$, $P^2$, $P^3$, and $P^4$ may have a substituent. Examples of the substituent include a halogeno group such as a fluoro group, a chloro group, a bromo group, or an iodo group; a hydroxyl group; a carboxyl group; a mercapto group; a sulfonic acid group; a nitro group; a phosphonic acid group; a silyl group including an alkyl group having 1 to 4 carbon atoms; a linear, branched, or cyclic saturated hydrocarbyl group having 1 to 50 carbon atoms in total, such as a methyl group, an ethyl group, a propyl group, an isopropyl group, a cyclopropyl group, a butyl group, an isobutyl group, a tert-butyl group, a pentyl group, a cyclopentyl group, a hexyl group, a cyclohexyl group, a norbornyl group, a nonyl group, a cyclononyl group, a decyl group, a 3,7-dimethyloctyl group, an adamantyl group, a dodecyl group, a cyclododecyl group, a pentadecyl group, an octadecyl group, or a docosyl group; a linear, branched, or cyclic alkoxy group having 1 to 50 carbon atoms in total, such as a methoxy group, an ethoxy group, a propyloxy group, a butoxy group, a pentyloxy group, a cyclohexyloxy group, a norbornyloxy group, a decyloxy group, or a dodecyloxy group; and a monovalent aromatic group having 6 to 60 carbon atoms in total, such as a phenyl group, a 4-methylphenyl group, a 1-naphthyl group, a 2-naphthyl group, or a 9-anthryl group. As the substituent, a halogeno group, a mercapto group, a hydroxyl group, a carboxyl group, a saturated hydrocarbyl group having 1 to 20 carbon atoms, a linear or branched alkoxy group having 1 to 10 carbon atoms in total, and a monovalent aromatic group having 6 to 30 carbon atoms in total are preferable; and a chloro group, a bromo group, a hydroxyl group, a carboxyl group, a methyl group, an ethyl group, a tert-butyl group, a cyclohexyl group, a norbornyl group, an adamantyl group, a methoxy group, an ethoxy group, and a phenyl group are more preferable.

In the Formula (1), the hydrocarbyl group represented by $R^\beta$ in the groups represented by $Z^1$ and $Z^2$ is the same group as the hydrocarbyl group represented by $R^\alpha$.

In the Formula (1), the structure as a combination of $P^5$ and $Z^1$ or the structure as a combination of $P^6$ and $Z^2$ are preferably structures represented by the following Formulae (3-a) to (3-t), more preferably structures represented by the following Formulae (3-a) to (3-h), even more preferably structures represented by the following Formulae (3-a) to (3-d), and particularly preferably a structure represented by the following Formula (3-a) or (3-b).

[Chemical Formula 12]

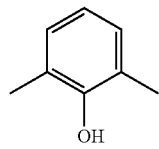
(3-a)

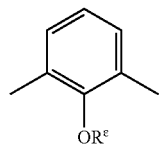
(3-b)

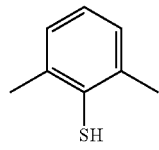
(3-c)

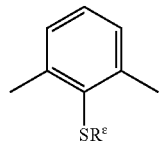
(3-d)

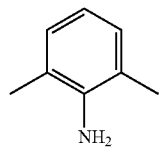
(3-e)

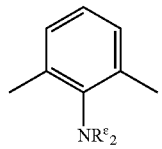
(3-f)

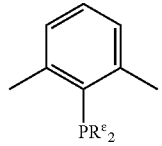
(3-g)

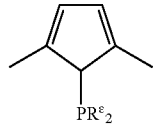
(3-h)

[Chemical Formula 13]

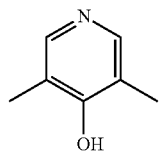
(3-i)

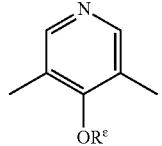
(3-j)

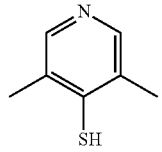
(3-k)

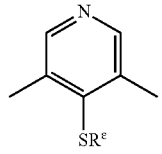
(3-l)

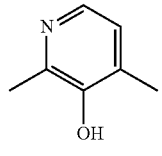
(3-m)

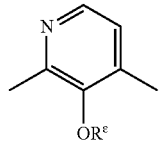
(3-n)

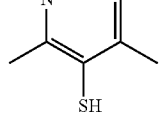
(3-o)

-continued (3-p)
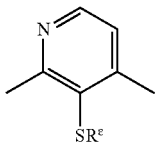

(3-q)
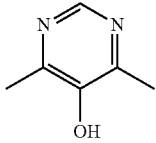

(3-r)
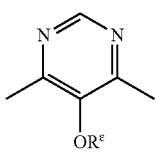

(3-s)
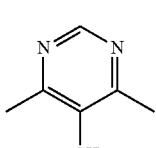

(3-t)
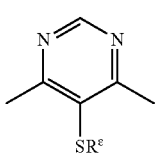

In the formulae, $R^\epsilon$ represents a hydrocarbyl group having 1 to 10 carbon atoms, and when there are a plurality of $R^\epsilon$s, these may be the same as or different from each other.

The aromatic ring and heterocyclic ring formed by $P^5$ and $P^6$ may have a substituent, and examples of the substituent include the same groups as the substituent that $P^1$ may have.

As the compound represented by the Formula (1), a compound is preferable in which the atomic group represented by $P^5$ binds to $Z^1$ to form a phenol structure, and the atomic group represented by $P^6$ binds to $Z^2$ to form a phenol structure.

As such a compound, a compound represented by the following Formula (2) is preferable since the metal complex is stabilized.

[Chemical Formula 14]

(2)
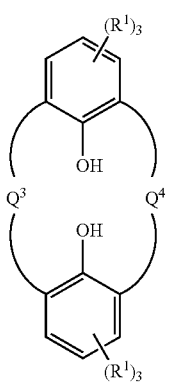

In Formula (2), $R^1$ represents a hydrogen atom or a monovalent group; a plurality of $R^1$s may be the same as or different from each other; $R^1$s may bind to each other to form a ring; each of $Q^3$ and $Q^4$ independently represents a divalent group represented by any of the following formulae:

[Chemical Formula 15]

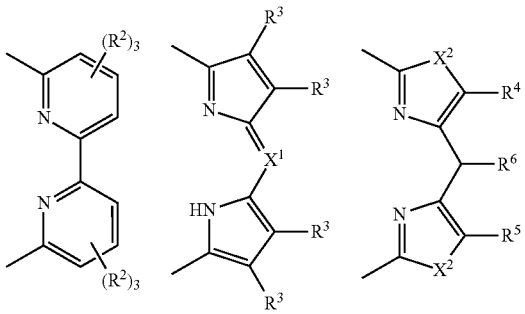

[In the formulae, $R^2$ represents a hydrogen atom or a monovalent group; a plurality of $R^2$s may be the same as or different from each other; $R^2$s may bind to each other to form a ring; $X^1$ represents a nitrogen atom or a trivalent group; $R^3$ represents a hydrogen atom or a monovalent group; a plurality of $R^3$s may be the same as or different from each other; $R^3$s may bind to each other to form a ring; $X^2$ represents a group represented by any of the following formulae:

[Chemical Formula 16]

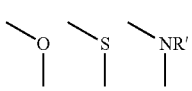

(In the formulae, R' represents a hydrogen atom or a hydrocarbyl group.); a plurality of $X^2$s may be the same as or different from each other; each of $R^4$, $R^5$, and $R^6$ independently represents a hydrogen atom or a monovalent group; $R^4$ and $R^6$ may bind to each other to form a ring; $R^5$ and $R^6$ may bind to each other to form a ring; and $R^4$, $R^5$, and $R^6$ may bind to one another to form a ring.]

In the Formula (2), examples of the monovalent group represented by $R^1$ include the same group as the monovalent group represented by $R^\delta$.

In the Formula (2), as the divalent group represented by $Q^3$ and $Q^4$, divalent groups represented by the following Formulae (4-a) to (4-j) are preferable; divalent groups represented by the following Formulae (4-a), (4-b), (4-d), (4-e), and (4-g) to (4-j) are more preferable; divalent groups represented by the following Formulae (4-a), (4-b), (4-d), (4-e), (4-h), and (4-j) are even more preferable; and divalent groups represented by the following Formulae (4-a), (4-b), (4-d), and (4-e) are particularly preferable.

[Chemical Formula 17]

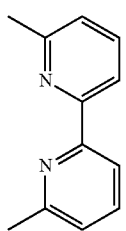 (4-a)

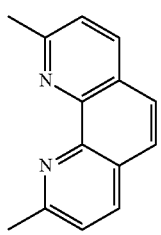 (4-b)

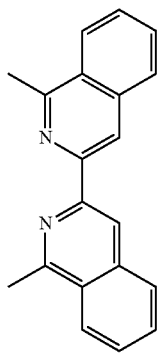 (4-c)

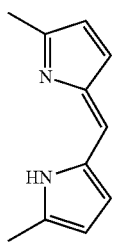 (4-d)

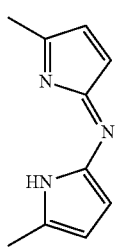 (4-e)

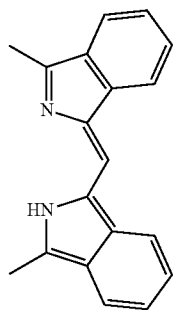 (4-f)

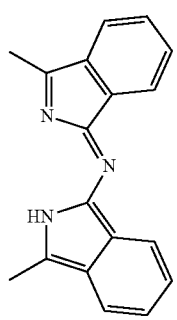 (4-g)

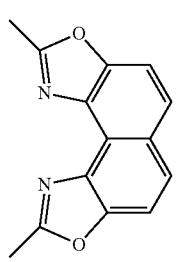 (4-h)

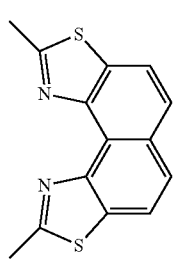 (4-i)

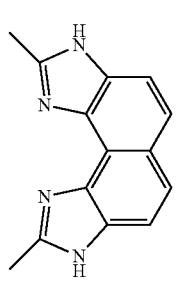 (4-j)

The divalent groups represented by Formulae (4-a) to (4-j) may have a substituent; and the substituent is the same group as the substituent that $P^1$ may have.]

Regarding $Q^3$ and $Q^4$, the monovalent group represented by $R^2$ in the formula is the same group as the group exemplified for $R^6$.

Regarding $Q^3$ and $Q^4$, examples of the trivalent group represented by $X^1$ in the formula include a methine group and a methine group substituted with a hydrocarbyl group.

Regarding $Q^3$ and $Q^4$, the monovalent group represented by $R^3$ in the formula is the same group as the group exemplified for $R^8$.

Regarding $Q^3$ and $Q^4$, the monovalent group represented by $R^4$, $R^5$, and $R^6$ in the formula is the same group as the group exemplified for $R^8$. $R^4$ and $R^6$ may bind to each other to form a ring, $R^5$ and $R^6$ may bind to each other to form a ring, and $R^4$, $R^5$, and $R^6$ may bind to one another to form a ring.

Examples of the compound represented by the Formula (2) include compounds represented by the following Formulae (5-a) to (5-i). Among these, compounds represented by the following Formulae (5-a) to (5-i) are preferable, compounds represented by the following Formulae (5-a) to (5-d) are more preferable, and compounds represented by the following Formulae (5-a) to (5-c) are even more preferable.

[Chemical Formula 18]

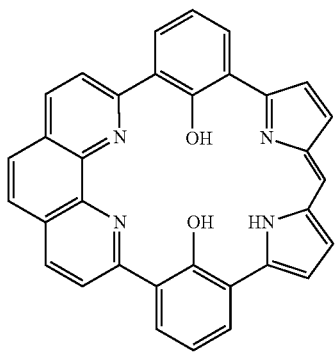

(5-a)

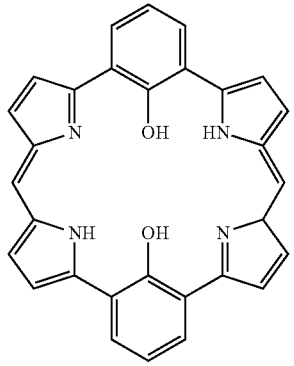

(5-b)

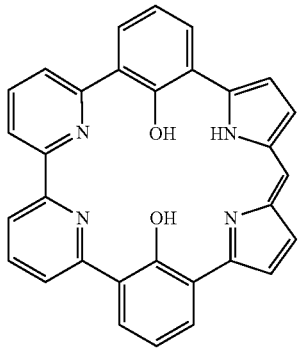

(5-c)

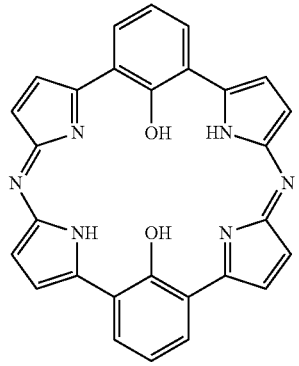

(5-d)

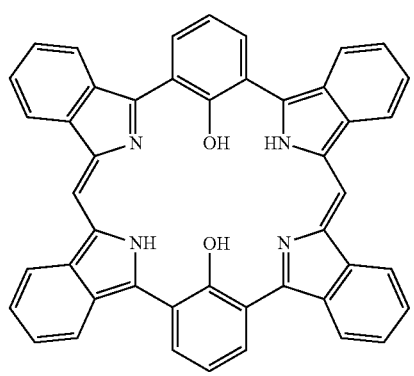

(5-e)

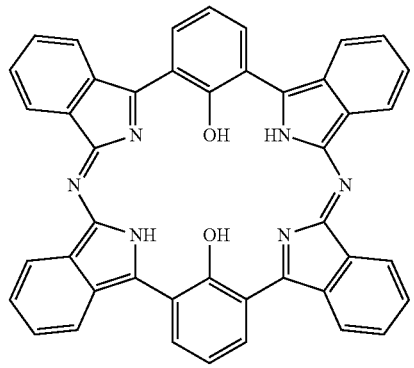

(5-f)

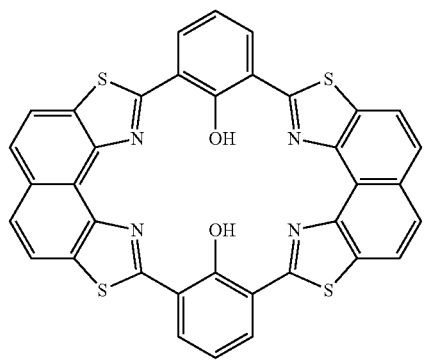

(5-g)

[Chemical Formula 19]

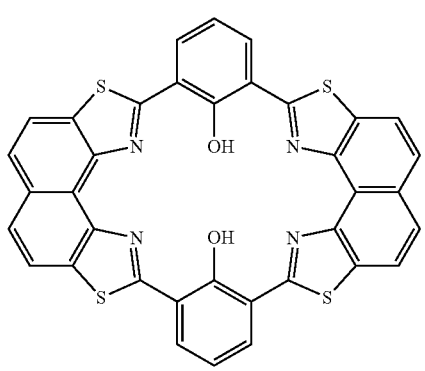
(5-h)

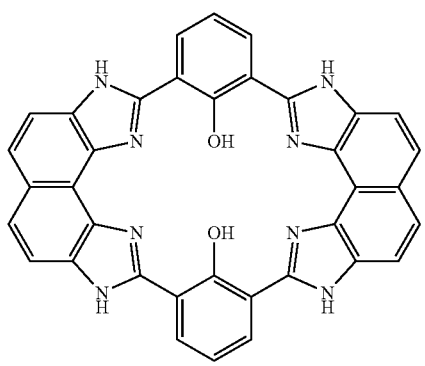
(5-i)

[Chemical Formula 20]

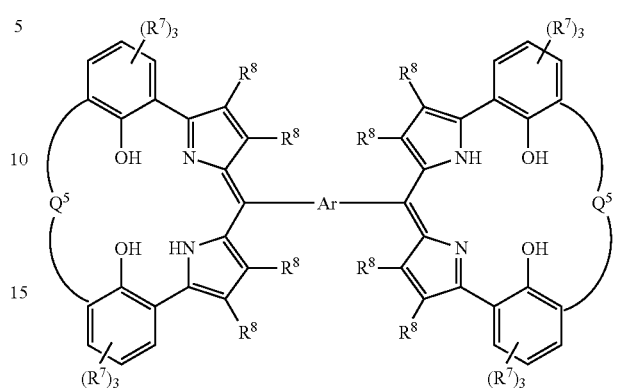
(3)

In Formula (3), each of $R^7$ and $R^8$ independently represents a hydrogen atom or a monovalent group; a plurality of $R^7$s may be the same as or different from each other; $R^7$s may bind to each other to form a ring; a plurality of $R^8$s may be the same as or different from each other; $R^8$s may bind to each other to form a ring; $Q^5$ represents a divalent group represented by any of the following formulae:

[Chemical Formula 21]

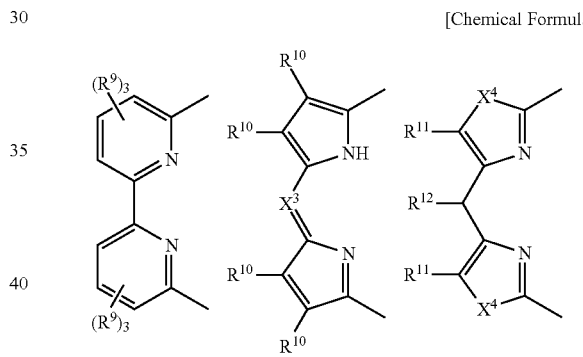

[In the formulae, $R^9$ represents a hydrogen atom or a monovalent group; a plurality of $R^9$s may be the same as or different from each other; $R^9$s may bind to each other to form a ring; $X^3$ represents a nitrogen atom or a trivalent group; $R^{10}$ represents a hydrogen atom or a monovalent group; a plurality of $R^{10}$s may be the same as or different from each other; $R^{10}$s may bind to each other to form a ring; $X^4$ represents a group represented by any of the following formulae:

[Chemical Formula 22]

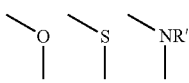

(In the formulae, R' represents a hydrogen atom or a hydrocarbyl group.); a plurality of $X^4$s may be the same as or different from each other; each of $R^{11}$ and $R^{12}$ independently represents a hydrogen atom or a monovalent group; $R^{11}$ and $R^{12}$ may bind to each other to form a ring.]; a plurality of $Q^5$s may be the same as or different from each other; and Ar represents a divalent aromatic group which may have a substituent.].

The compounds represented by Formulae (5-a) to (5-i) may have a substituent, and the substituent is the same as the substituent that $P^1$ may have.

The "divalent aromatic group" constituting the compound of the present invention refers to an atomic group that remains after two hydrogen atoms are removed from an aromatic ring as a monocyclic ring or a condensed ring.

Examples of the divalent aromatic group constituting the compound of the present invention include a divalent aromatic group having 6 to 20 carbon atoms in total, such as a 1,4-phenylene group, a 2,7-triphenylene group, a 1,5-naphthylene group, a 2,6-naphthylene group, a 1,5-anthrylene group, a 9,10-anthrylene group, a 2,7-pyrenylene group, a 2,7-phenanthrene group, or a 3,8-phenanthrolene group. Among these, a 1,4-phenylene group, a 1,5-naphthylene group, a 2,6-naphthylene group, a 1,5-anthrylene group, a 9,10-anthrylene group, and a 9,10-anthrylene group are preferable, since the obtained compound is stabilized in the atmosphere. The divalent aromatic group may have a substituent.

As the compound of the present invention, a compound represented by the following Formula (3) is preferable since it can be easily synthesized.

In the Formula (3), examples of the monovalent group represented by $R^7$, $R^8$, $R^9$, $R^{10}$, $R^{11}$, and $R^{12}$ include the same group as the monovalent group represented by $R^\delta$.

In the formula relating to $Q^5$, examples of the trivalent group represented by $X^3$ include a methine group and a methine group substituted with a hydrocarbyl group. Examples of the hydrocarbyl group include the same group as the hydrocarbyl group represented by $R^\alpha$.

In the Formula (3), examples of the divalent aromatic group which is represented by Ar and may have a substituent include the same group described above.

In the Formula (3), the hydrocarbyl group represented by R' in the divalent group represented by $Q^5$ is the same group as the hydrocarbyl group represented by $R^\alpha$.

As the compound represented by the Formula (3), compounds represented by the following Formulae (I-1) to (I-11) are preferable, compounds represented by the following Formulae (I-1) to (I-7) are more preferable, and compounds represented by the following Formulae (I-1) to (I-4) are even more preferable.

[Chemical Formula 23]

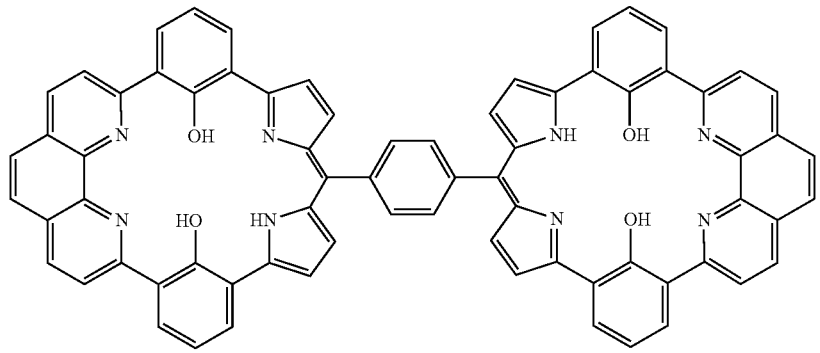

(I-1)

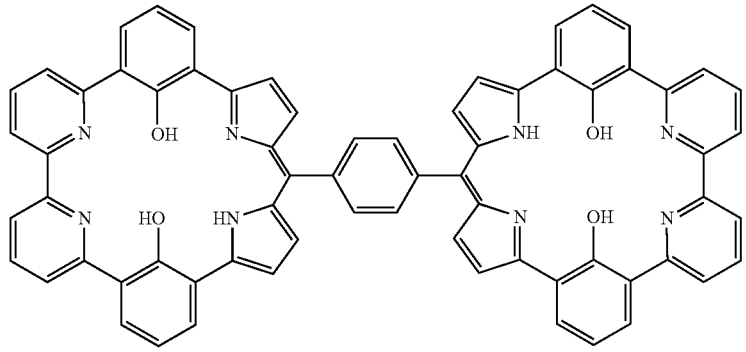

(I-2)

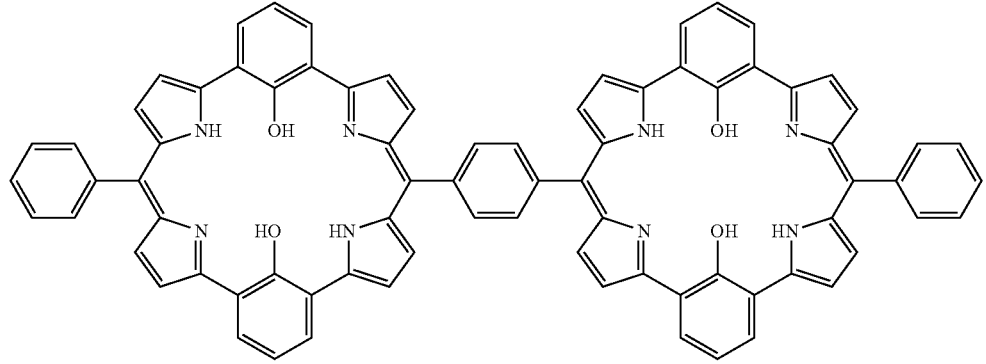

(I-3)

(I-4)
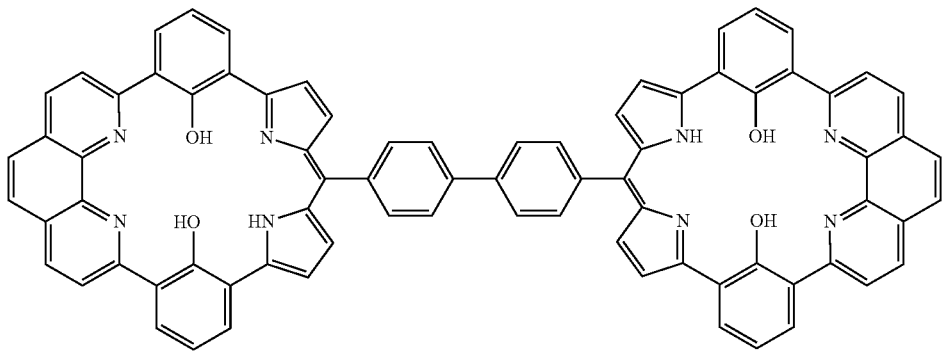
(I-5)
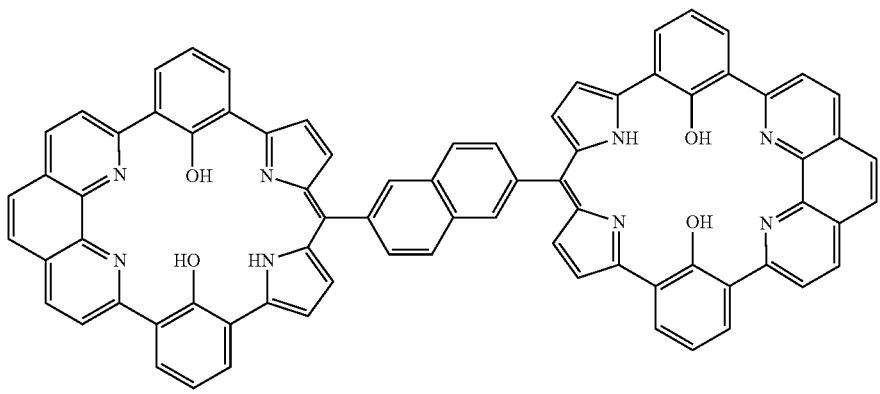
[Chemical Formula 24]
(I-6)
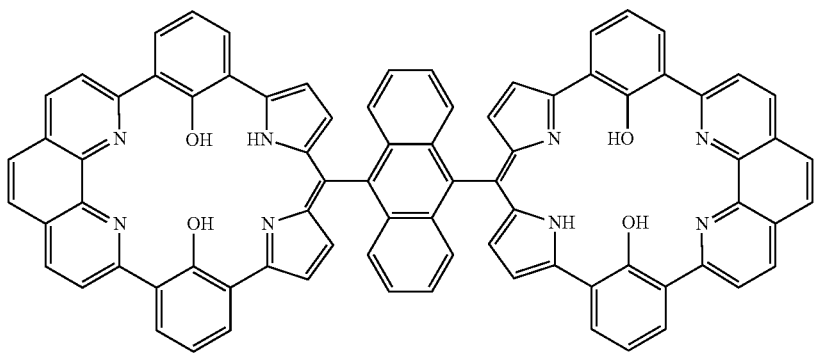
(I-7)
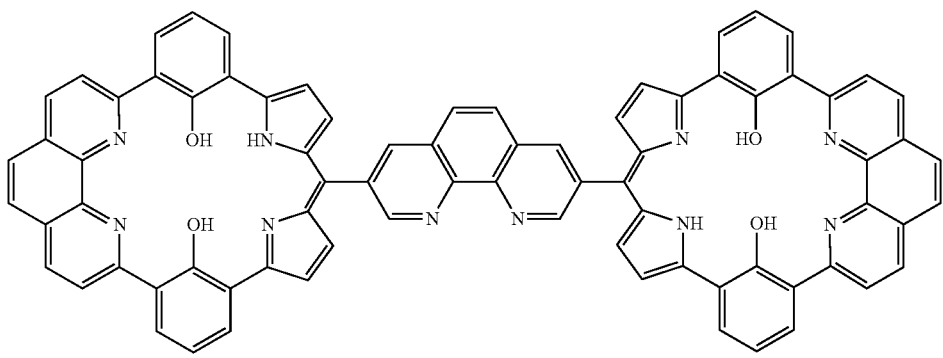

-continued

[Chemical Formula 25]

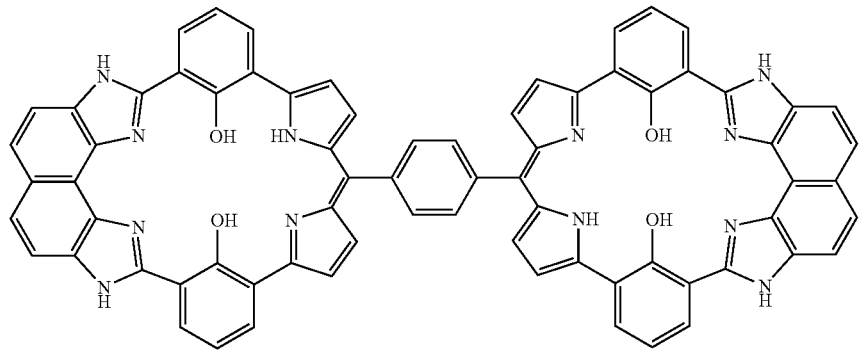

(I-8)

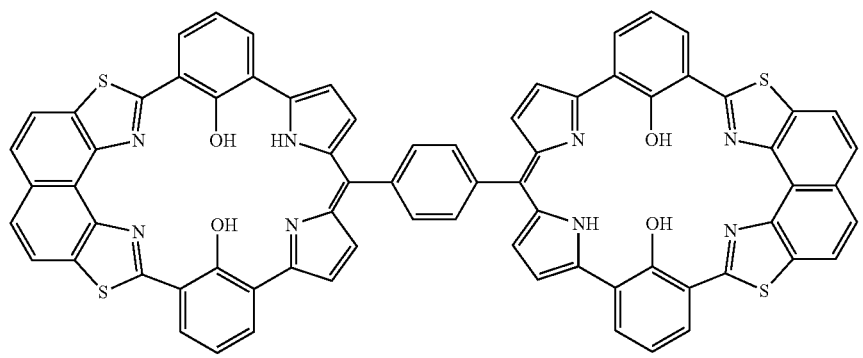

(I-9)

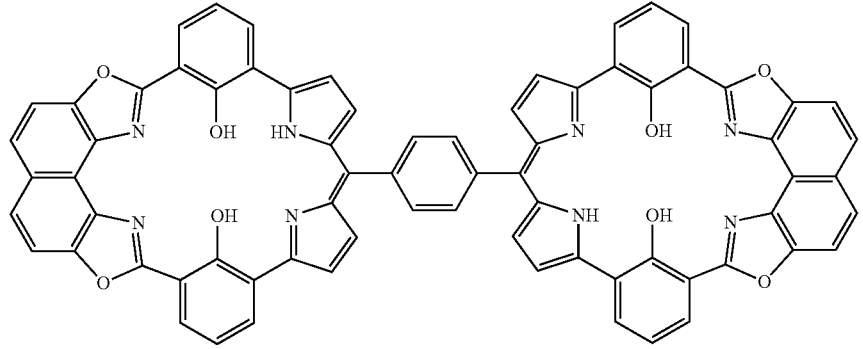

(I-10)

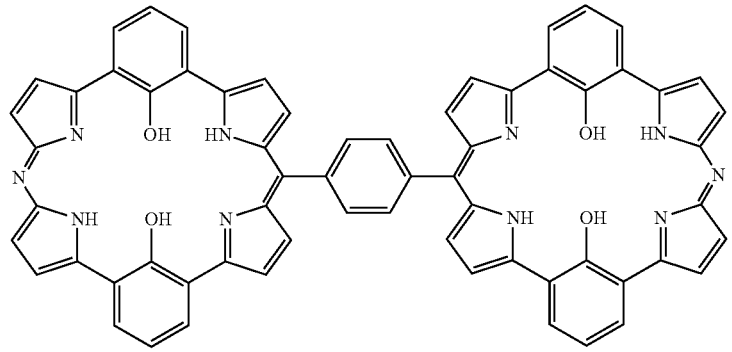

(I-11)

The compounds represented by Formulae (I-1) to (I-11) may have a substituent, and the substituent is the same group as the substituent that $P^1$ may have.]

The compound of the present invention can be synthesized in a manner disclosed in, for example, Tetrahedron., 1995, 55, 8377, in which a reaction for adding an organometallic reagent to a heterocyclic compound, an oxidation reaction, and a halogenation reaction are performed, and then a cross-coupling reaction using a transition metal catalyst is performed to synthesize a precursor, followed by a ring-closing reaction is performed using an aldehyde. In addition, the compound of the present invention can also be synthesized by adding an aldehyde to a compound having a pyrrolyl group on the terminal so as to cause the pyrrolyl group to bind to a methylene group.

Among the compounds of the present invention, the compound represented by Formula (3) is taken as an example to describe the synthesis method. It is preferable that the compound represented by Formula (3) be synthesized by a reaction between a compound represented by the following Formula (4) and an aldehyde represented by the following Formula (5) (see the following reaction scheme

[Chemical Formula 26]

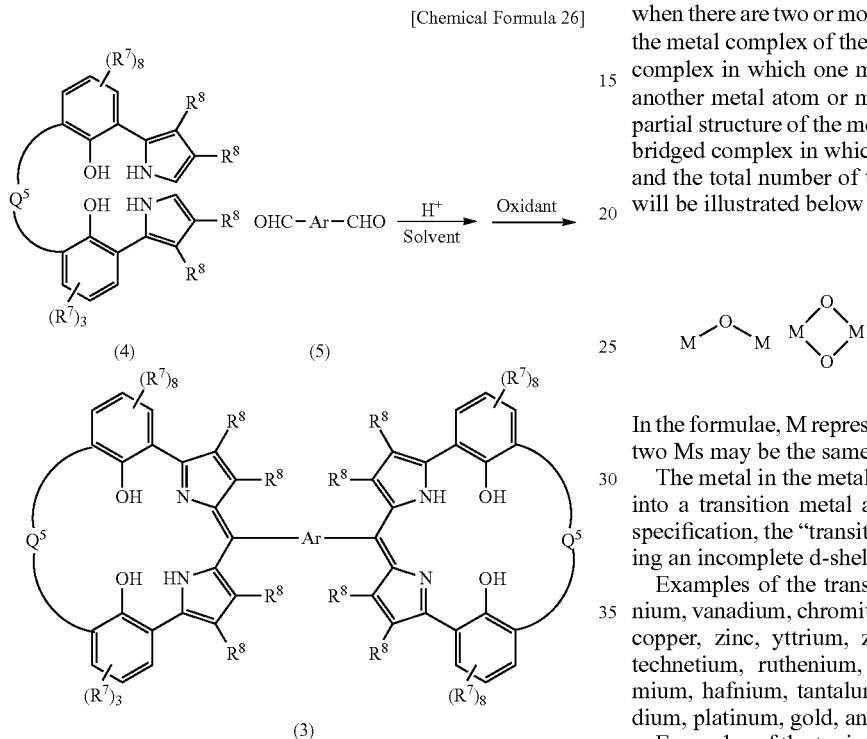

In the formulae, $R^7$, $R^8$, $Q^5$, and Ar have the same definition as described above.

The above reaction can be performed by dissolving a raw material in an appropriate solvent by using an acid as a catalyst. At this time, the acid itself may be used as the solvent.

Examples of the acid include an organic acid such as acetic acid, propionic acid, or butanoic acid; boron trifluoride; boron trifluoride etherate; boron trichloride; boron tribromide; trifluoroacetic acid; trifluoromethane sulfonic acid; and p-toluene sulfonic acid.

When the acid itself is used as a solvent, the above organic acid is preferable as the acid.

Examples of the solvent include dichloromethane, chloroform, carbon tetrachloride, methanol, ethanol, and a combination of these.

The temperature of the above reaction is generally 0° C. to 250° C., preferably 0° C. to 200° C., and particularly preferably 0° C. to 160° C.

The time of the reaction is generally 1 minute to 1 week, preferably 5 minutes to 100 hours, and particularly preferably 1 hour to 72 hours.

The reaction temperature and reaction time can be adjusted according to the combination of the acid and solvent.

In the reaction, an oxidant that is easily available in general, such as oxygen, p-chloranil, or 2,3-dichloro-5,6-dicyano-1,4-benzoquinone, can be added.

Next, the metal complex of the present invention will be described.

The metal complex of the present invention is a metal complex including a metal atom or a metal ion and a ligand which is the compound described above.

In the metal complex of the present invention, the number of the metal atom or metal ion is generally 1 to 4 and preferably 2 to 4.

In the metal complex of the present invention, the metal atom or the metal ion forms a bond (generally, a coordinate bond) with a hetero atom of the compound as a ligand. Herein, when there are two or more metal atoms or metal ions in total, the metal complex of the present invention may be a bridged complex in which one metal atom or metal ion is linked to another metal atom or metal ion via a bridging ligand. The partial structure of the metal atom and an oxygen atom in the bridged complex in which a hetero atom is an oxygen atom, and the total number of the metal atoms and metal ions is 2 will be illustrated below for example.

[Chemical Formula 27]

$$M\!-\!\!\overset{O}{\underset{}{}}\!\!-\!M \qquad M\overset{O}{\underset{O}{\rightleftarrows}}M$$

In the formulae, M represents a metal atom or a metal ion, and two Ms may be the same as or different from each other.

The metal in the metal atom or metal ion can be classified into a transition metal and a typical metal. In the present specification, the "transition metal" refers to an element having an incomplete d-shell or an f-sub-shell.

Examples of the transition metal include scandium, titanium, vanadium, chromium, manganese, iron, cobalt, nickel, copper, zinc, yttrium, zirconium, niobium, molybdenum, technetium, ruthenium, rhodium, palladium, silver, cadmium, hafnium, tantalum, tungsten, rhenium, osmium, iridium, platinum, gold, and mercury.

Examples of the typical metal include aluminum, gallium, germanium, indium, tin, antimony, thallium, lead, and bismuth.

Among these metals, transition metals belonging to the fourth to sixth periods are preferable since the catalytic performance becomes excellent. Among these, titanium, vanadium, manganese, iron, cobalt, nickel, copper, zinc, molybdenum, ruthenium, rhodium, palladium, silver, tantalum, tungsten, rhenium, osmium, iridium, platinum, and gold are more preferable; manganese, iron, cobalt, nickel, copper, and platinum are even more preferable; and iron, cobalt, and copper are particularly preferable.

The metal complex of the present invention may contain at least one kind of constituent element selected from a group consisting of neutral molecules and counterions making the metal complex electrically neutral.

The neutral molecules are molecules forming solvated salts by being solvated, and examples thereof include compounds excluding the above compounds (for example, the compound represented by the Formula (3)). Specific examples thereof include water, methanol, ethanol, n-propanol, isopropyl alcohol, 2-methoxyethanol, 1,1-dimethylethanol, ethylene glycol, N,N'-dimethylformamide, N,N'-dimethylacetamide, N-methyl-2-pyrrolidone, dimethylsulfoxide, acetone, chloroform, acetonitrile, benzonitrile, triethylamine, pyridine, pyrazine, diazabicyclo[2,2,2]octane, 4,4'-bipyridine, tetrahydrofuran, diethyl ether, dimethoxyethane, methyl ethyl ether, 1,4-dioxane, and the like. Preferable examples of the neutral molecules include water, methanol, ethanol, isopropyl alcohol, ethylene glycol, N,N'-dimethylformamide, N,N'-dimethylacetamide, N-methyl-2-pyrrolidone, chloroform, acetonitrile, benzonitrile, triethylamine, pyridine, pyrazine, diazabicyclo[2,2,2]octane, 4,4'-bipyridine, tetrahydrofuran, dimethoxyethane, and 1,4-dioxane. In addition, the metal complex of the present invention may contain only one neutral molecule or two or more of thereof.

When the metal complex is a complex ion, as a counterion forming a complex salt with the metal complex, a cation or an anion making the metal complex electrically neutral is selected.

When the complex ion is charged positively, examples of the counterion include a fluoride ion, a chloride ion, a bromide ion, an iodide ion, a sulfide ion, an oxide ion, a hydroxide ion, a hydride ion, a sulfite ion, a phosphate ion, a cyanide ion, an acetate ion, a carbonate ion, a sulfate ion, a nitrate ion, a hydrogen carbonate ion, a trifluoroacetate ion, a thiocyanide ion, a trifluoromethane sulfonate ion, acetylacetonate, a tetrafluoroborate ion, a hexafluorophosphate ion, a tetraphenyl borate ion, and the like. Among these, a chloride ion, a bromide ion, an iodide ion, an oxide ion, a hydroxide ion, a hydride ion, a phosphate ion, a cyanide ion, an acetate ion, a carbonate ion, a sulfate ion, a nitrate ion, acetylacetonate, and tetraphenyl borate ion are preferable. Moreover, when there are a plurality of counterions, these may be the same as or different from each other. In addition, the neutral molecule may coexist with the ion.

When the complex ion is charged negatively, examples of the counterion include alkali metal ions; alkali earth metal ions; tetraalkyl ammonium ions such as a tetra(n-butyl)ammonium ion and a tetraethyl ammonium ion; and tetraaryl phosphonium ions such as a tetraphenyl phosphonium ion. Among these, a lithium ion, a sodium ion, a potassium ion, a rubidium ion, a cesium ion, a magnesium ion, a calcium ion, a strontium ion, a barium ion, a tetra(n-butyl)ammonium ion, a tetraethyl ammonium ion, and a tetraphenyl phosphonium ion are preferable; a tetra(n-butyl)ammonium ion, a tetraethyl ammonium ion, and a tetraphenyl phosphonium ion are more preferable; and a tetra(n-butyl)ammonium ion and a tetraethyl ammonium ion are even more preferable.

Examples of the metal complex of the present invention include compounds represented by the following Formulae (6-aa) to (6-ll), and specifically, the examples include compounds represented by the following Formulae (6-a) to (6-g).

[Chemical Formula 28]

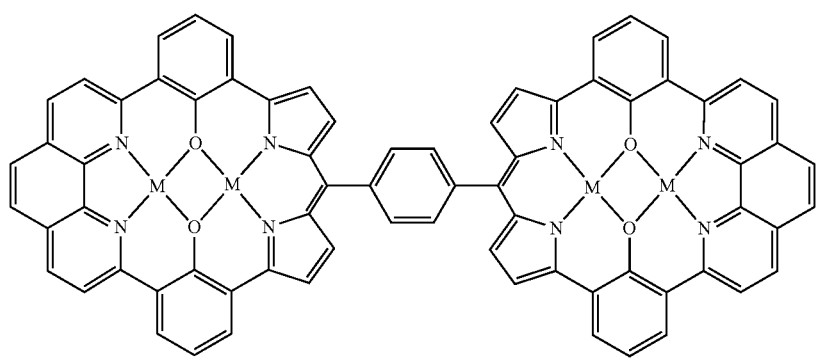

(6-aa)

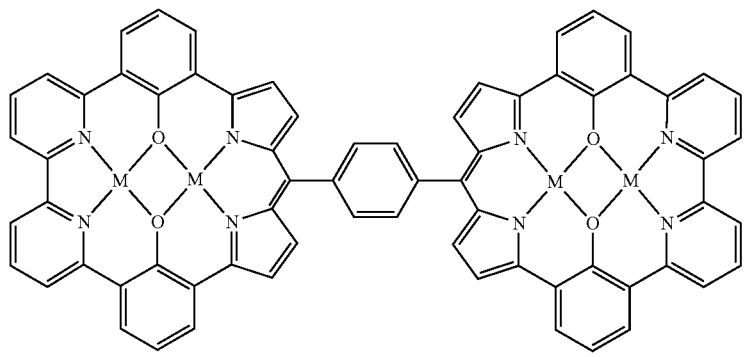

(6-bb)

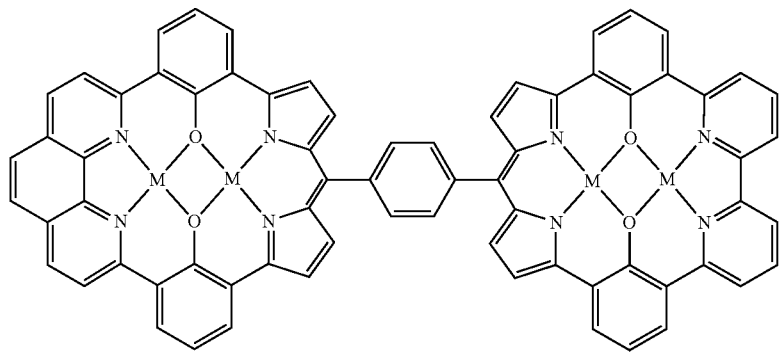
(6-cc)
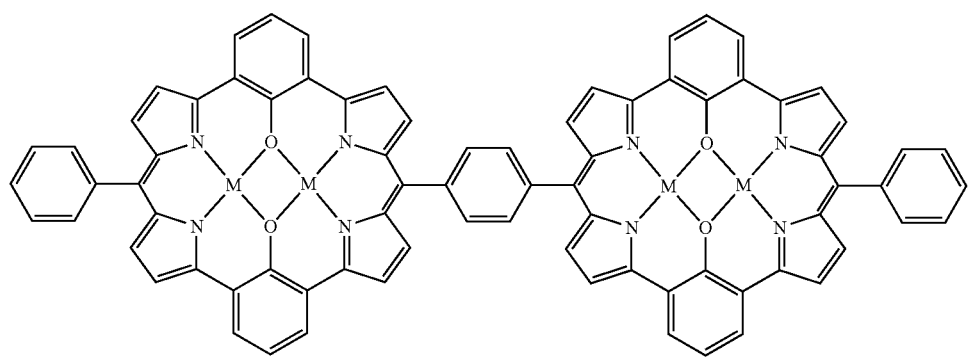
(6-dd)
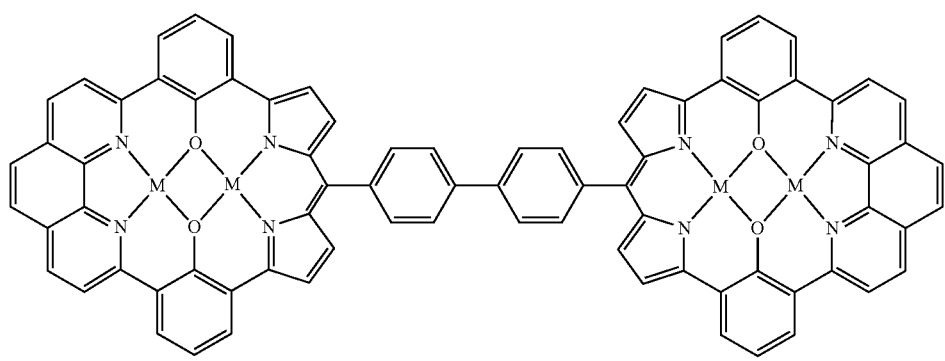
(6-ee)
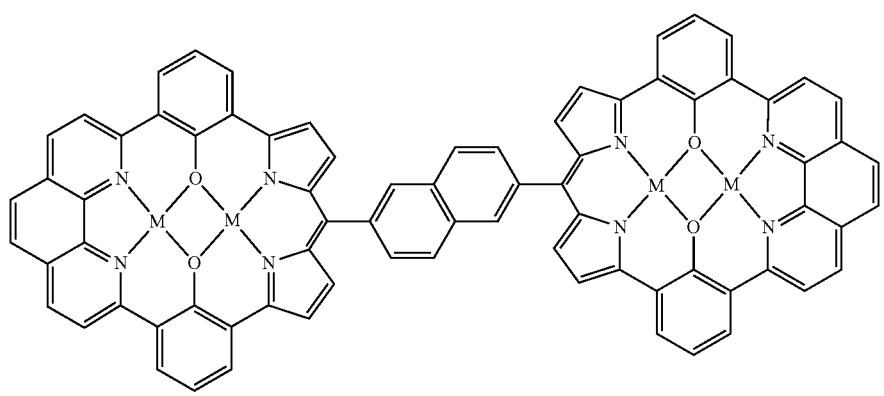
(6-ff)

[Chemical Formula 29]
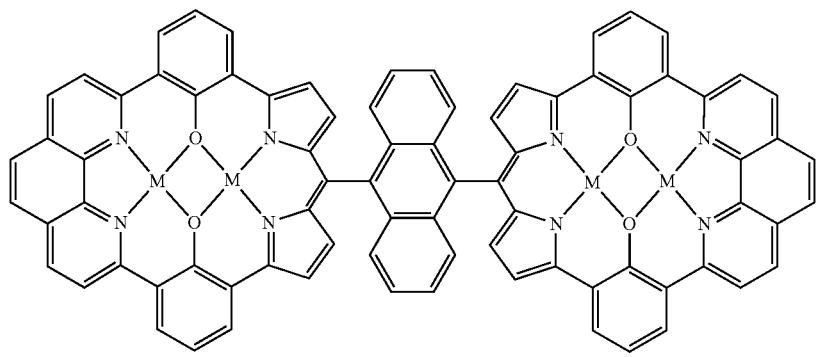
(6-gg)
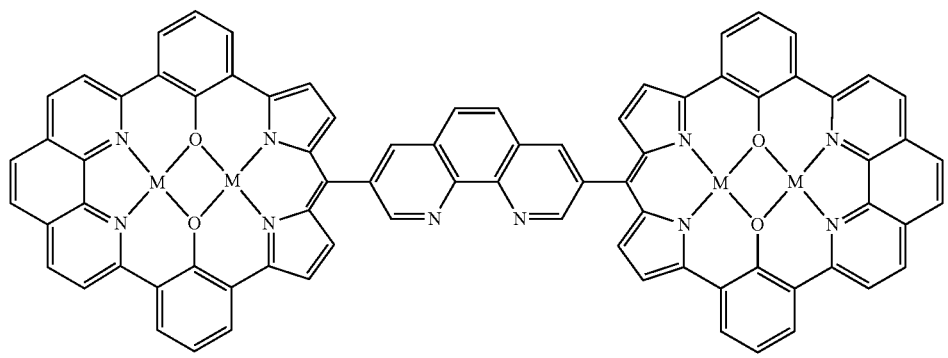
(6-hh)
[Chemical Formula 30]
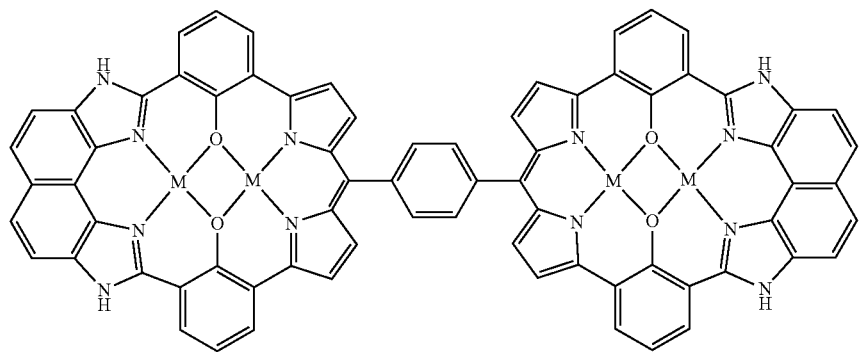
(6-ii)
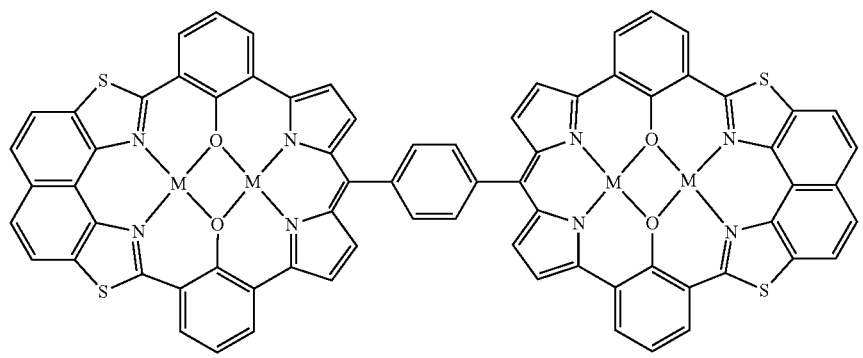
(6-jj)

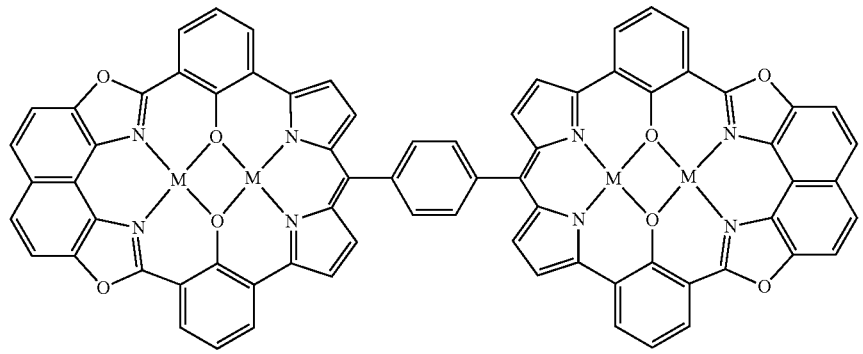

(6-kk)

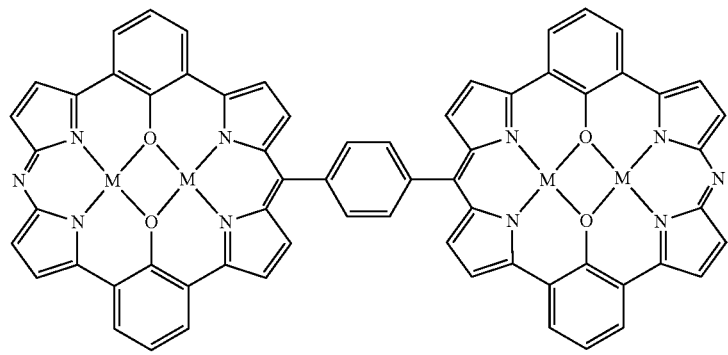

(6-ll)

In Formulae (6-aa) to (6-ll), M represents a metal atom or a metal ion; a plurality of Ms may be the same as or different from each other; the above compounds may have a substituent; the substituent is the same group as the substituent that P¹ may have; and as described above, the above compounds may contain at least one kind of constituent element selected from a group consisting of counterions and neutral molecules.

[Chemical Formula 31]

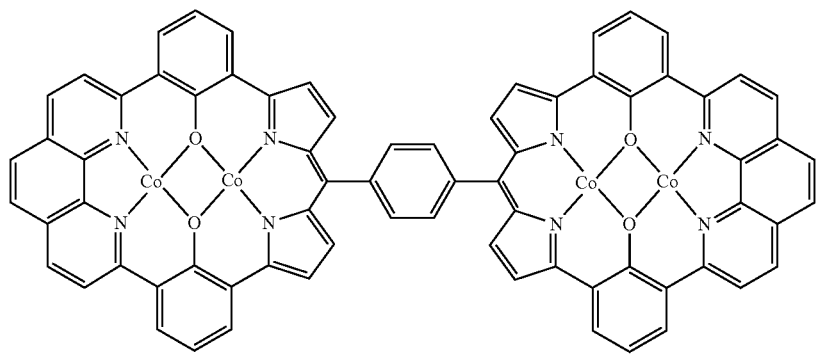

(6-a)

-continued
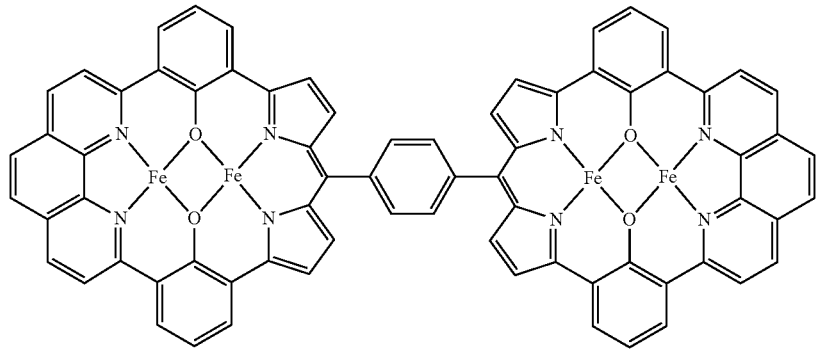
(6-b)
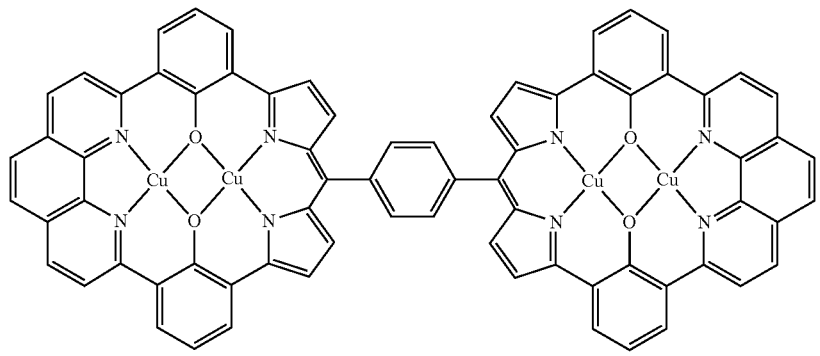
(6-c)
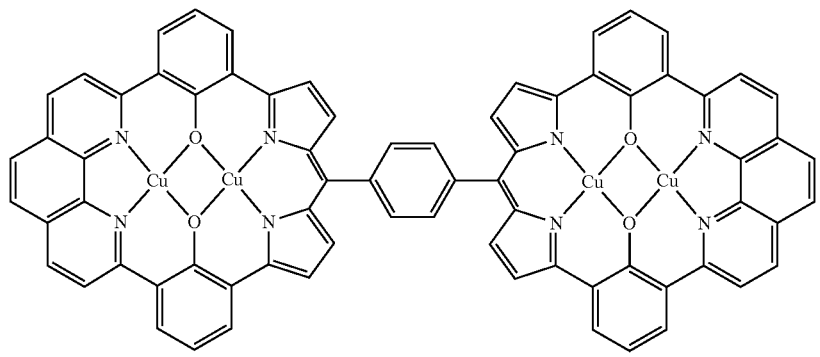
(6-d)
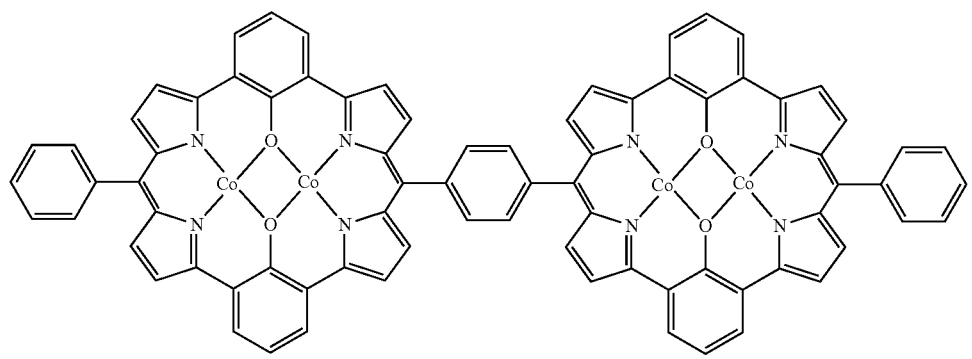
(6-e)

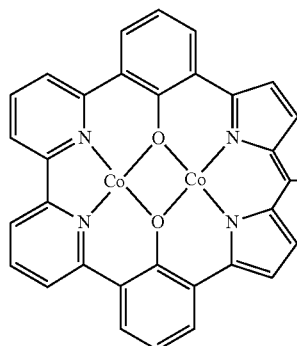
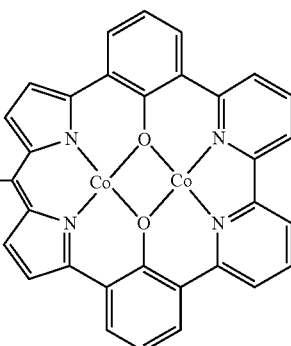

(6-f)

The compounds represented by Formulae (6-a) to (6-f) may have a substituent; the substituent is the same group as the substituent that $P^1$ may have; and as described above, the above compounds may contain at least one kind of constituent element selected from a group consisting of counterions and neutral molecules.

Next, the synthesis method of the metal complex of the present invention will be described.

The metal complex of the present invention can be obtained by, for example, a method in which the compound of the present invention is synthesized in an organochemical manner, and then the obtained compound is mixed and reacted with a reagent (hereinafter, sometimes called a "metal-imparting agent") for imparting metal ions. The amount of the metal-imparting agent to be reacted may be adjusted according to the target metal complex. However, generally, the amount is preferably much larger than that of the ligand.

Examples of the metal-imparting agent include acetate, fluoride, chloride, bromide, iodide, sulfate, carbonate, nitrate, hydroxide, perchlorate, trifluoroacetate, trifluoromethane sulfonate, tetrafluoroborate, hexafluorophosphate, and tetraphenyl borate of the above metal, and among these, acetate of the metal is preferable. Examples of the acetate include cobalt(II) acetate, iron(II) acetate, manganese(II) acetate, manganese(III) acetate, nickel(II) acetate, copper(II) acetate, and zinc(II) acetate; and among these, cobalt(II) acetate, iron (II) acetate, and copper(II) acetate are preferable.

The metal-imparting agent may be a hydrate, and examples thereof include cobalt(II) acetate tetrahydrate, manganese(II) acetate tetrahydrate, manganese(III) acetate dihydrate, nickel (II) acetate tetrahydrate, copper(II) acetate monohydrate, and zinc(II) acetate dihydrate.

The above reaction is preferably performed in the presence of a solvent (that is, a reaction solvent).

Examples of the solvent include water, acetic acid, aqueous ammonia, methanol, ethanol, n-propanol, isopropyl alcohol, 2-methoxyethanol, 1-butanol, 1,1-dimethylethanol, ethylene glycol, diethylether, 1,2-dimethoxyethane, methyl ethyl ether, 1,4-dioxane, tetrahydrofuran, benzene, toluene, xylene, mesitylene, durene, decalin, dichloromethane, chloroform, carbon tetrachloride, chlorobenzene, 1,2-dichlorobenzene, N,N'-dimethylformamide, N,N'-dimethylacetamide, N-methyl-2-pyrrolidone, dimethyl sulfoxide, acetone, acetonitrile, benzonitrile, triethylamine, and pyridine.

One kind of these solvents may be used alone, or two or more kinds thereof may be used concurrently. However, a solvent dissolving the compound of the present invention and the metal-imparting agent is preferable.

The temperature of the reaction is generally −10° C. to 200° C., preferably 0° C. to 150° C., and particularly preferably 0° C. to 100° C.

The time of the reaction is generally 1 minute to 1 week, preferably 5 minutes to 24 hours, and particularly preferably 1 hour to 12 hours.

The reaction temperature and reaction time can be adjusted according to the type of the compound of the present invention and the metal-imparting agent.

After the reaction ends, in order to isolate and purify the generated metal complex from the reaction solution, known means such as recrystallization, reprecipitation, and chromatography can be used alone or used in combination.

In addition, depending on the type of the solvent, sometimes the generated metal complex is precipitated. The precipitated metal complex is separated by filtration or the like and optionally washed or dried, whereby the metal complex can be isolated and purified.

Next, the modified compound of the present invention will be described.

The modified compound of the present invention can be obtained by heating a mixture including the metal complex and a carbon support. The metal complex of the present invention is made into a modified compound in this manner, whereby the solubility thereof in water can be lowered. Moreover, one kind of the metal complex and the carbon support may be used alone, or two or more kinds thereof may be used concurrently.

Examples of the carbon support include carbon particles such as Norit, Ketjen black, Vulcan, black pearl, and acetylene black; fullerene such as C60 and C70; carbon nanotubes; carbon nanohorns; and carbon fiber. Among these, Ketjen black, Vulcan, acetylene black, carbon nanotubes, and fullerene are preferable; Ketjen black, Vulcan, and carbon nanotubes are more preferable; and Ketjen black and Vulcan are even more preferable.

In the mixing ratio between the metal complex and the carbon support in the above mixture, the amount of the metal complex is preferably 5% by mass to 70% by mass, more preferably 10% by mass to 60% by mass, and particularly preferably 15% by mass to 50% by mass, based on the total mass of the metal complex and the carbon support.

Before the heating is performed, it is preferable that the mixture be dried for 6 hours or longer at a temperature of 15°

C. to 200° C., as a pretreatment. For the pretreatment, a vacuum drier or the like can be used.

Examples of the atmosphere for performing the heating include hydrogen, helium, nitrogen, ammonia, oxygen, neon, argon, krypton, xenon, acetonitrile, and a mixed gas of these. Among these, hydrogen, helium, nitrogen, ammonia, oxygen, neon, argon, and mixed gas of these are preferable; and hydrogen, nitrogen, ammonia, argon, and mixed gas of these are more preferable.

The lower limit of the heating temperature is generally 600° C., preferably 700° C., and more preferably 800° C. The upper limit thereof is generally 1200° C., preferably 1100° C., and more preferably 1000° C.

That is, the heating temperature is generally from 600° C. to 1200° C., preferably from 700° C. to 1100° C., and more preferably from 800° C. to 1000° C.

The heating time may be adjusted according to the atmosphere, temperature, and the like at the time of performing the heating.

In the heating step, while the gas is being sealed or allowed to circulate, the temperature may be slowly increased from room temperature and then immediately decreased after the temperature reaches a desired value. However, after the temperature reaches a desired value, if it is kept as is to slowly heat the metal complex, this is preferable since the durability can be further improved. The temperature is kept generally for 10 minutes to 100 hours, preferably for 30 minutes to 40 hours, more preferably for 1 hour to 10 hours, and even more preferably for 1 hour to 3 hours.

The heating can be performed using a device such as an oven, a furnace, or an IH hotplate.

The heating may be performed until a mass reduction ratio before and after heating (that is, a reduction ratio of the mass of the modified compound obtained after heating to the mass of the mixture before heating) preferably becomes 5% or higher, more preferably becomes 10% or higher, and particularly preferably becomes 15% or higher. Moreover, the upper limit of the decrease ratio of mass is preferably 50%, more preferably 40%, and particularly preferably 30%.

That is, the heating may be performed until the mass reduction ratio before and after heating preferably becomes 5% to 50%, more preferably becomes 10% to 40%, and particularly preferably becomes 15% to 30%.

Moreover, the upper limit of the carbon content is preferably 99% by mass, more preferably 97% by mass, and particularly preferably 95% by mass.

That is, the heating may be performed such that the carbon content in the modified compound preferably becomes 40% by mass to 99% by mass, more preferably becomes 60% by mass to 97% by mass, and particularly preferably becomes 80% by mass to 95% by mass.

The metal complex and modified compound of the present invention may be used as they are individually. However, they may be used as a composition by being combined with other components. Herein, examples of those other components include the carbon support and a polymer. The first composition of the present invention is a composition containing the metal complex and at least one kind of component selected from a group consisting of the carbon support and the polymer. The composition is preferably a composition substantially containing the metal complex and at least one kind of component selected from a group consisting of the carbon support and the polymer. The second composition of the present invention is a composition containing the modified compound and the polymer, and preferably is a composition substantially containing the modified compound and the polymer. In addition, the first and second compositions of the present invention (hereinafter, these will be sometimes collectively called the "composition of the present invention") are generally solid contents. Moreover, in the composition of the present invention, each of the components may be used alone, or two or more kinds thereof may be used concurrently.

In the first composition of the present invention, the content of the carbon support is generally 100 parts by mass to 10000 parts by mass and preferably 200 parts by mass to 600 parts by mass, based on 100 parts by mass of the metal complex of the present invention.

In the first composition of the present invention, the content of the polymer is generally 50 parts by mass to 500 parts by mass and preferably 100 parts by mass to 300 parts by mass, based on 100 parts by mass of the metal complex of the present invention.

In the second composition of the present invention, the content of the polymer is generally 10 parts by mass to 200 parts by mass and preferably 20 parts by mass to 100 parts by mass, based on 100 parts by mass of the modified compound of the present invention.

As the polymer, Nafion (registered trademark), polyvinylidene fluoride, polyether ether ketone, polysulfone, polyether sulfone, poly(arylene/ether), polyimide, polyphenylene sulfide, polyphenyl quinoxalene, polyphenylene, polyphenylene vinylene, polyfluorene, polyethylene, polypropylene, polybutadiene, polyisoprene, polyvinyl chloride, polystyrene, polyacrylonitrile, polybenzimidazole, polyaniline, polypyrrole, polythiophene, polypyridine, and compounds obtained by introducing a sulfonic acid group into these polymers are preferable.

Next, the usefulness of the metal complex, modified compound, and composition of the present invention (hereinafter, sometimes called the "metal complex and the like of the present invention") will be described.

The metal complex and the like of the present invention can be used for organic synthesis by acting as a catalyst (that is, a redox catalyst) in a redox reaction accompanying electron transfer, such as an oxygenation reaction, an oxidative coupling reaction, a dehydrogenation reaction, a hydrogenation reaction, or an oxide decomposition reaction, or can be utilized for uses such as an additive, a modifier, a battery, a material of sensor, an electroluminescence material, and the like.

It is preferable that the metal complex and the like of the present invention be used as a redox catalyst. Specifically, they used as a decomposition catalyst for hydrogen peroxide, an oxidative polymerization catalyst for aromatic compounds, a catalyst for purifying exhaust gas/waste water, an oxidation-reduction catalyst layer of a dye-sensitized solar cell, a reduction catalyst for carbon dioxide, a catalyst for producing reformed hydrogen, an oxygen sensor, and the like.

Particularly, though a water-soluble metal complex and the like are easily effused in a reaction accompanying water, the metal complex and the like of the present invention do not easily dissolve in water since they are coupled, and as a result, effusion thereof is inhibited.

Moreover, the metal complex and the like of the present invention are also useful as a luminescence material of organic EL elements and an organic semiconductor material of organic transistors, dye-sensitized solar cells, and the like.

EXAMPLES

Hereinafter, the present invention will be described based on examples

Example 1

Synthesis of Compound (A)

[Chemical Formula 32]

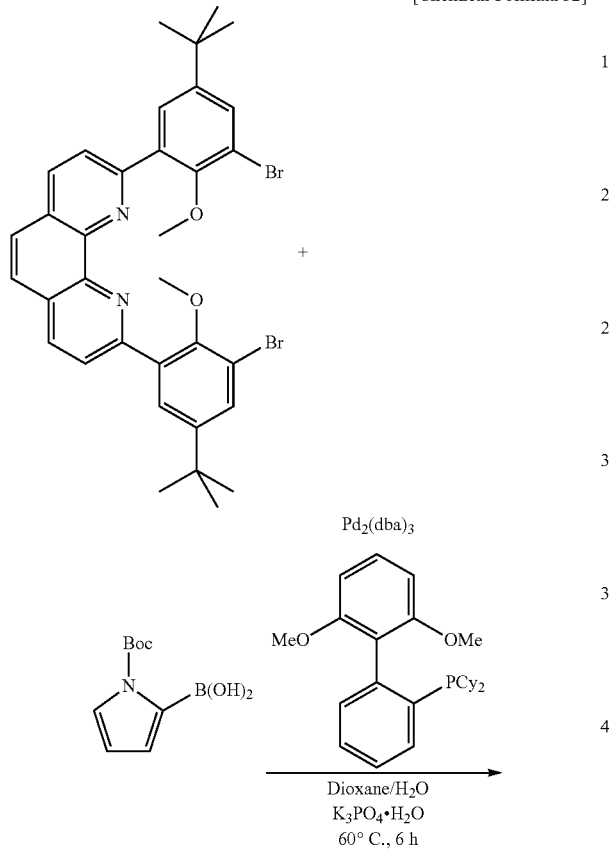

Compound (A)

In the formula, Me represents a methyl group, and Boc represents a tert-butoxycarbonyl group.

In an argon atmosphere, 3.945 g of 2,9-bis(3'-bromo-5'-tert-butyl-2'-methoxyphenyl)-1,10-phenanthroline, 3.165 g of 1-N-Boc-pyrrole-2-boronic acid, 0.138 g of tris(benzylideneacetone)dipalladium ($Pd_2(dba)_3$), 0.247 g of 2-cyclohexylphosphino-2',6'-dimethoxybiphenyl, and 5.527 g of potassium phosphate were dissolved in a mixed solvent containing 200 mL of dioxane and 20 mL of water, followed by stirring for 6 hours at 60° C. After the reaction ended, the reaction liquid was left to cool, and then distilled water and chloroform were added thereto to extract an organic layer. The obtained organic layer was concentrated, and as a result, a black residue was obtained. The residue was purified with a silica gel column, thereby obtaining a compound (A).

The obtained compound (A) was subjected to instrumental analysis, and the results were as follows.

$^1$H-NMR (300 MHz, $CDCl_3$) δ (ppm)=1.34 (s, 18H), 1.37 (s, 18H), 3.30 (s, 6H), 6.21 (m, 2H), 6.27 (m, 2H), 7.37 (m, 2H), 7.41 (s, 2H), 7.82 (s, 2H), 8.00 (s, 2H), 8.19 (d, J=8.6 Hz, 2H), 8.27 (d, j=8.6 Hz, 2H).

Synthesis of Compound (B)

[Chemical Formula 33]

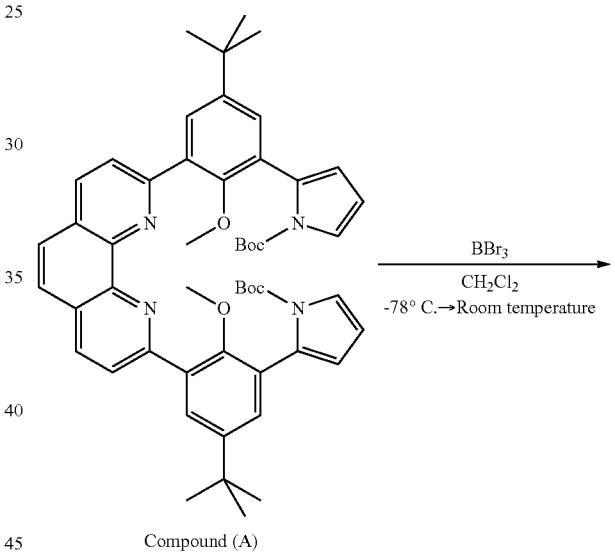

Compound (A)

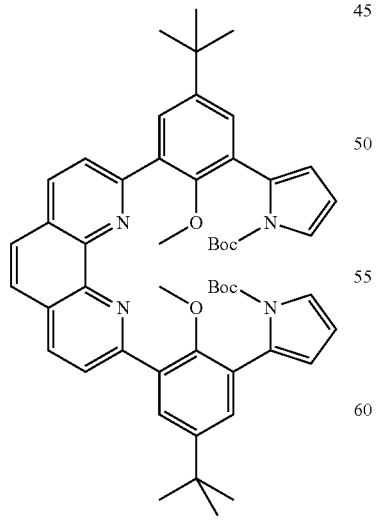

Compound (A)

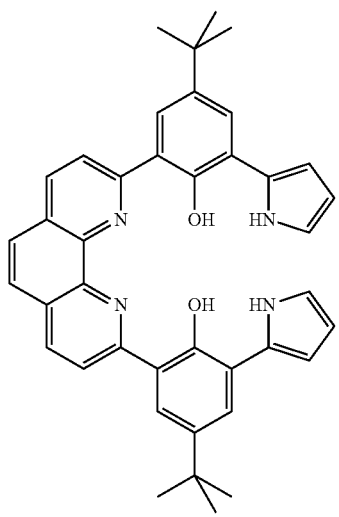

Compound (B)

In a nitrogen atmosphere, 0.904 g of the compound (A) was dissolved in 10 mL of dichloromethane. While the dichloromethane solution was being cooled at −78° C., 8.8 mL of boron tribromide (1.0 M dichloromethane solution) was slowly added dropwise thereto. After the dropwise addition, the solution was stirred as it was for 10 minutes and then left under stirring until the temperature reached room temperature. 3 hours later, the reaction liquid was cooled to 0° C., and an aqueous saturated sodium hydrogen carbonate solution was added thereto. Thereafter, chloroform was added thereto to perform extraction, the organic layer was concentrated, and as a result, a brown residue was obtained. The residue was purified with a silica gel column, thereby obtaining a compound (B).

The obtained compound (B) was subjected to instrumental analysis, and the results were as follows.

$^1$H-NMR (300 MHz, CDCl$_3$) δ (ppm)=1.40 (s, 18H), 6.25 (m, 2H), 6.44 (m, 2H), 6.74 (m, 2H), 7.84 (s, 2H), 7.89 (s, 2H), 7.92 (s, 2H), 8.35 (d, J=8.4 Hz, 2H), 8.46 (d, J=8.4 Hz, 2H), 10.61 (s, 2H), 15.88 (s, 2H).

Synthesis of Compound (C)

[Chemical Formula 34]

In a nitrogen atmosphere, 0.121 g of the compound (B) and 0.013 g of terephthalaldehyde were dissolved in 30 mL of dichloromethane. A drop of trifluoroacetic acid was added thereto, followed by stirring for 24 hours at room temperature. Subsequently, 0.050 g of chloranil was added thereto, followed by stirring for 24 hours. Thereafter, the reaction liquid was concentrated, and the thus obtained black residue was washed with chloroform and methanol in this order, thereby obtaining a compound (C).

The obtained compound (C) was subjected to instrumental analysis, and the result was as follows.

ESI-MS[M+H]$^+$: 1307.5

Example 2

Synthesis of Metal Complex (D)

was stirred for 5 hours while being heated at 80° C. The obtained solution was solidified by being concentrated and dried, and as a result, a green solid was obtained. The solid was washed with water, thereby obtaining a metal complex (D).

The obtained compound (D) was subjected to instrumental analysis, and the result are as follows.

ESI-MS [M-2(CH$_3$COO)]$^{2+}$: 768.2

Example 3

Preparation of Composition (E)

The metal complex (D) and a carbon support (Ketjen black EC600JD, manufactured by Lion Corporation) were mixed with each other in a mass ration of 1:4, and the obtained

[Chemical Formula 35]

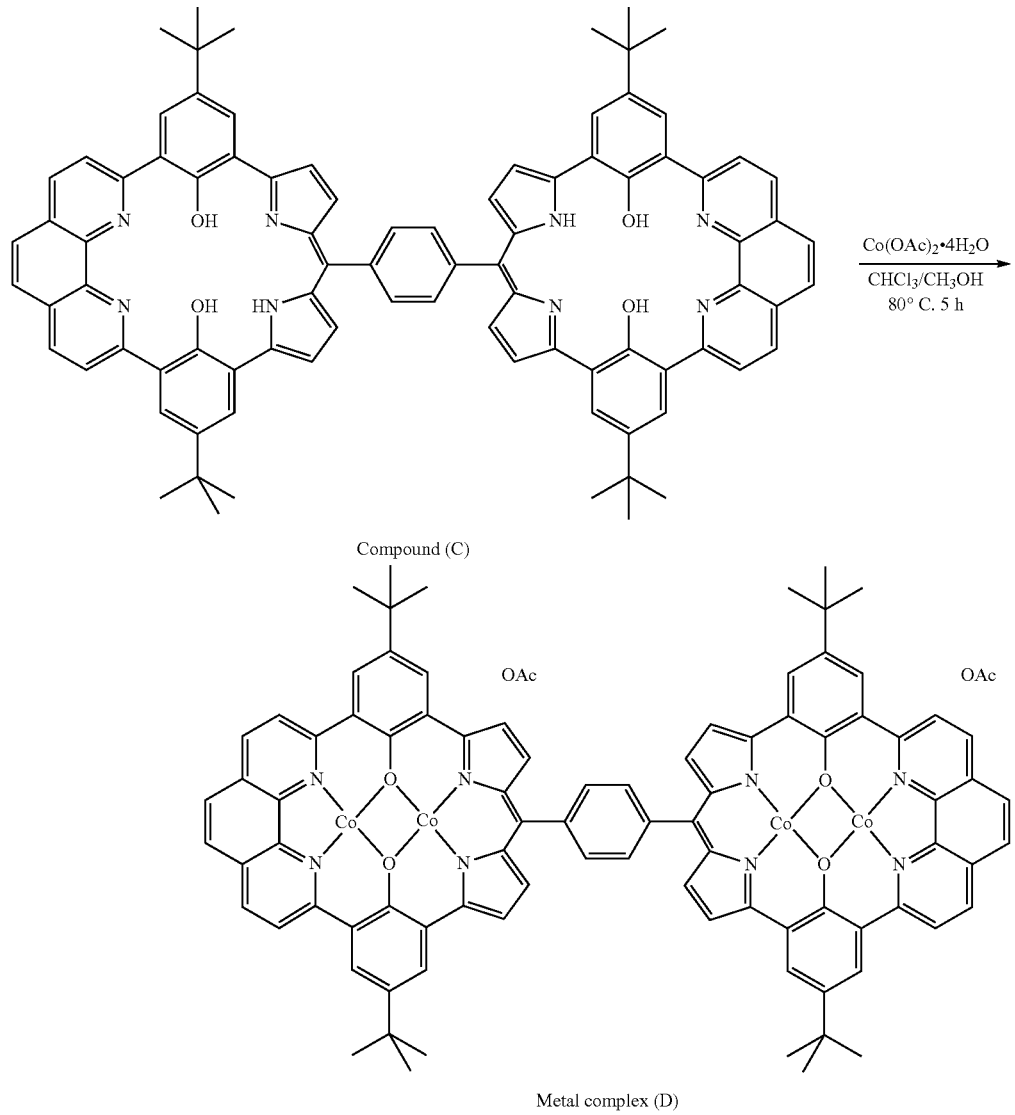

In a nitrogen atmosphere, a mixed solution containing 0.047 g of the compound (C), 3 mL of methanol including 0.018 g of cobalt acetate tetrahydrate, and 3 mL of chloroform mixture was stirred in methanol at room temperature. Thereafter, the mixture was dried for 12 hours under a pressure reduced to 200 Pa, thereby preparing a composition (E).

Example 4

Preparation of Modified Compound (F)

The composition (E) was heated for 2 hours at 800° C. in a nitrogen atmosphere by using a tubular furnace, thereby obtaining a modified compound (F). The mass reduction ratio before and after heating and the carbon content of the modified compound (F) are shown in Table 1. Moreover, the tubular furnace used for heating and the heating conditions are shown below.

Tubular furnace: a program-controllable opening/closing type tubular furnace EPKRO-14R, manufactured by Isuzu Seisakusho Co., Ltd.

Heating conditions

Atmosphere: nitrogen gas flow (200 ml/min)

Temperature increasing/decreasing rate: 200° C./hr

TABLE 1

|  | Mass reduction ratio (%) | Carbon content (% by mass) |
|---|---|---|
| Modified compound (F) | 17.9 | 91.2 |

Comparative Example 1

In a nitrogen atmosphere, 0.061 g of the compound (B) and 0.012 g of benzaldehyde were dissolved in 5 mL of propionic acid, followed by heating for 7 hours at 140° C. Thereafter, the propionic acid was evaporated, and the obtained black residue was purified with a silica gel column, thereby obtaining a compound (G).

The obtained compound (G) was subjected to instrumental analysis, and the results were as follows.

$^1$H-NMR (300 MHz, CDCl$_3$) δ (ppm)=1.49 (s, 18H), 6.69 (d, J=4.8 Hz, 2H), 7.01 (d, J=4.8 Hz, 2H), 7.57 (m, 5H), 7.90 (s, 4H), 8.02 (s, 2H), 8.31 (d, J=8.1 Hz, 2H), 8.47 (d, J=8.1 Hz, 2H)

[Chemical Formula 36]

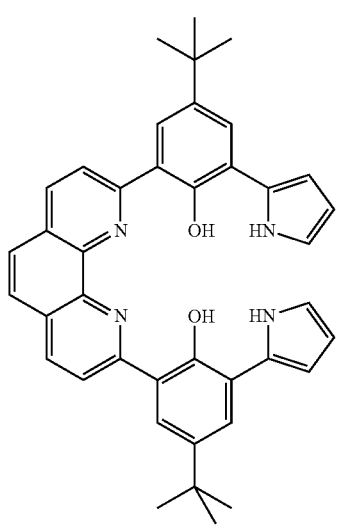

Compound (B)

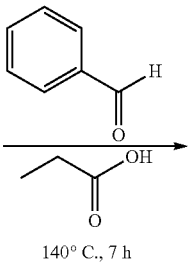

140° C., 7 h

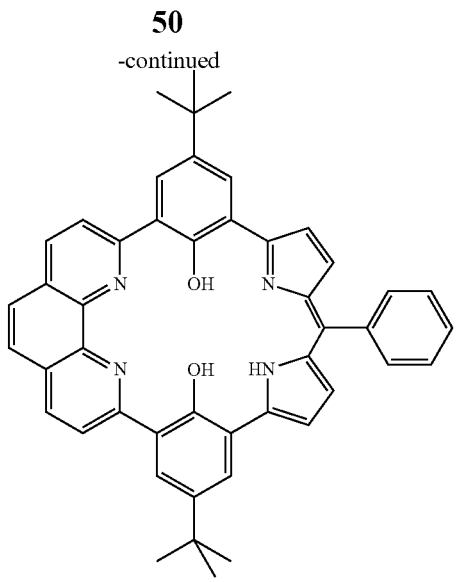

Compound (G)

[Chemical Formula 37]

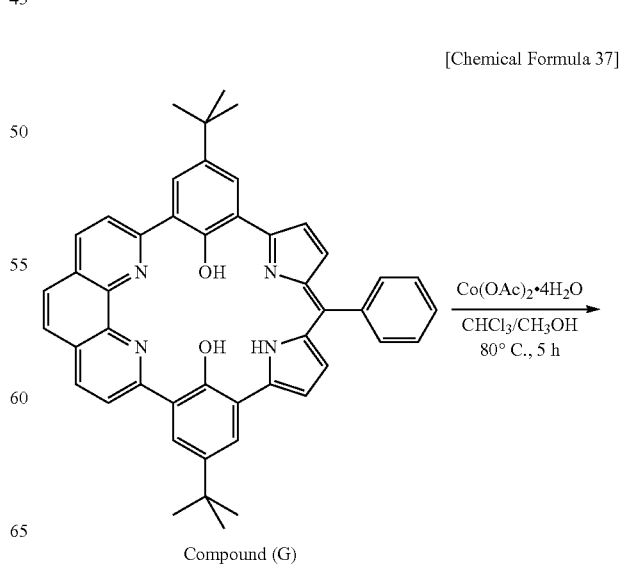

Compound (G)

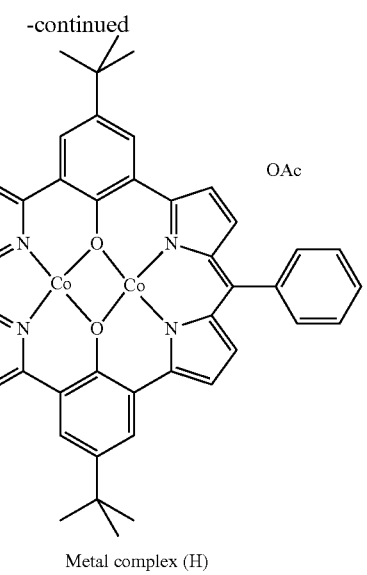

Metal complex (H)

In a nitrogen atmosphere, a mixed liquid containing 0.045 g of the compound (G), 3 mL of methanol including 0.040 g of cobalt acetate tetrahydrate, and 3 mL of chloroform was stirred for 5 hours while being heated at 80° C. The obtained solution was solidified by being concentrated and dried, and as a result, a blue solid was obtained. The blue solid was washed with water, thereby obtaining a metal complex (H).

The obtained metal complex (H) was subjected to instrumental analysis, and the result are as follows.

ESI-MS [M+•]: 866.0

Moreover, the metal complex (H) and a carbon support (Ketjen black EC600JD, manufactured by Lion Corporation) were mixed with each other in a mass ration of 1:4, and the obtained mixture was stirred in methanol at room temperature. Thereafter, the mixture was dried for 12 hours under a pressure reduced to 200 Pa, thereby preparing a comparative composition (I).

Thereafter, a comparative modified compound (J) was obtained in the same manner as in Example 4, except that the composition (E) was changed to the comparative composition (I) in Example 4.

<Evaluation>

(Evaluating Oxygen Reduction Ability by Using Rotating Ring-Disk Electrode)

As an electrode, a ring-disk electrode in which a disk portion is formed of glassy carbon (diameter 4.0 mm), and a ring portion is formed of platinum (inner diameter of ring of 5.0 mm, outer diameter of ring of 7.0 mm) was used. 0.6 mL of distilled water, 0.4 mL of ethanol, and 20 μL of a Nafion solution (manufactured by Sigma-Aldrich Co. 5% by mass solution) were added to a sample bottle containing 2 mg of the composition (E), modified compound (F), comparative composition (I), or comparative modified compound (J), and then the resultant was dispersed with ultrasonic waves for 30 minutes. 4.44 μL of the obtained suspension was added dropwise to the disk portion of the electrode, and then the resultant was dried overnight at room temperature, thereby preparing an electrode for measurement. The electrode prepared in this manner was rotated to measure the current value of an oxygen reduction reaction caused at this time. The measurement was performed in a nitrogen atmosphere and an oxygen atmosphere at room temperature. A current value obtained by the measurement performed in the nitrogen atmosphere was subtracted from a current value obtained by the measurement performed in the oxygen atmosphere, and the thus obtained value was taken as a current value of oxygen reduction. This current value was divided by the surface area of the disk portion, and the thus obtained value was taken as a current density. The current density at a potential of 0.4 V (vs RHE (reversible hydrogen electrode)) in the oxygen atmosphere is described in Table 2. In addition, the measurement instruments and measurement conditions are as follows.

Measurement Instruments

PRDE-2 rotating ring/disk electrode apparatus and ALS model 701C dual electrochemical analyzer manufactured by BAS Inc.

Measurement Conditions

Cell solution: 0.05 mol/L aqueous sulfuric acid solution (oxygen saturation)

Solution temperature: 25° C.

Reference electrode: silver/silver chloride electrode (saturated KCl)

Counter electrode: platinum wire

Sweep rate: 5 mV/s

Rotating speed of electrode: 2400 rpm

TABLE 2

|  | Metal complex | Carbon support | Polymer | Current density (mA/cm$^2$) |
|---|---|---|---|---|
| Composition (E) | Metal complex (D) 100 parts by mass | 400 parts by mass | 250 parts by mass | 2.88 |
| Modified compound (F) | Modified compound (F) 100 parts by mass | 0 part by mass | 50 parts by mass | 3.11 |
| Comparative composition (1) | Metal complex (H) 100 parts by mass | 400 parts by mass | 250 parts by mass | 2.58 |
| Comparative modified compound (J) | Modified compound (J) 100 parts by mass | 0 part by mass | 50 parts by mass | 2.34 |

The current density of the composition (E) prepared in examples is higher than that of the comparative composition (I) prepared in comparative examples, so the oxygen reduction ability of the composition (E) is high.

The current density of the modified compound (F) prepared in examples is higher than that of the comparative modified compound (J) prepared in comparative examples, so the oxygen reduction ability of the modified compound (F) is high.

<Evaluation>

[Solubility Test]

Each of the metal complex (D) and the metal complex (H) was taken by 1 mg and put in a vial, and then 1 ml of water was added thereto, followed by stirring. After 1 hour, the metal complex (D) did not dissolve. However, a portion of the metal complex (H) dissolved, and the color of water turned pale blue.

Therefore, it was found that the metal complex (D) containing a coupled compound as a ligand is insoluble in water.

INDUSTRIAL APPLICABILITY

The present invention can provide an electrode catalyst having a high degree of redox ability, and a metal complex and a compound useful for producing the electrode catalyst. Accordingly, the present invention is extremely useful industrially.

The invention claimed is:
1. A metal complex comprising:
a metal atom or a metal ion; and
a ligand, the ligand being a compound represented by the following Formula (3):

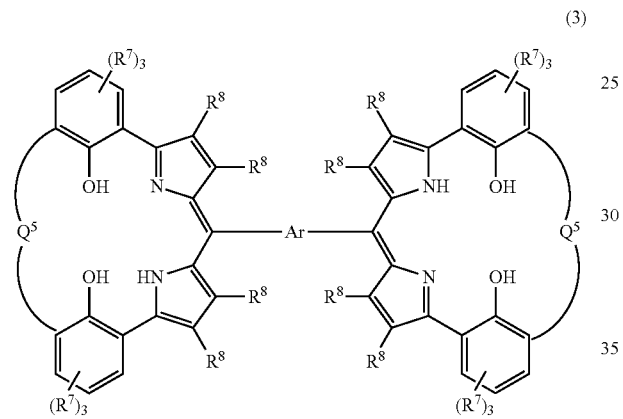

wherein $R^7$ and $R^8$ represents a hydrogen atom or a monovalent group;
a plurality of $R^7$s are optionally the same as or different from each other; $R^7$s may bind to each other to form a ring;
a plurality of $R^8$s are optionally the same as or different from each other; $R^8$s optionally bind to each other to form a ring;
$Q^5$ represents a divalent group represented by any of the following formulae:

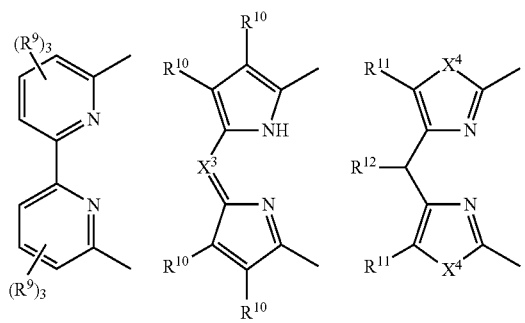

wherein $R^9$ represents a hydrogen atom or a monovalent group; a plurality of $R^9$s are optionally the same as or different from each other; $R^9$s optionally bind to each other to form a ring;
$X^3$ represents a nitrogen atom or a trivalent group;
$R^{10}$ represents a hydrogen atom or a monovalent group; a plurality of $R^{10}$s are optionally the same as or different from each other; $R^{10}$s optionally bind to each other to form a ring;
$X^4$ represents a group represented by any of the following formulae:

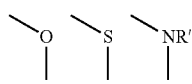

wherein R' represents a hydrogen atom or a hydrocarbyl group;
a plurality of $X^4$s are optionally the same as or different from each other;
each of $R^{11}$ and $R^{12}$ independently represents a hydrogen atom or a monovalent group; $R^{11}$ and $R^{12}$ optionally bind to each other to form a ring;
a plurality of $Q^5$s are optionally the same as or different from each other; and
Ar represents a divalent aromatic group which optionally has a substituent.

2. The metal complex according to claim 1,
wherein the metal in the metal atom or the metal ion is a transition metal belonging to the fourth to sixth periods on the periodic table.

3. The metal complex according to claim 2,
wherein the metal of the metal atom or the metal ion is manganese, iron, cobalt, nickel, copper, or platinum.

4. The metal complex according to claim 1,
wherein the number of the metal atom or the metal ion is 1 to 4.

5. The metal complex according to claim 1,
wherein, in the formula (3), Ar represents a 1,4-phenylene group, a 2,7-triphenylene group, a 1,5-naphthylene group, a 2,6-naphthylene group, a 1,5-anthrylene group, a 9,10-anthrylene group, a 2,7-pyrenylene group, a 2,7-phenanthrene group, or a 3,8-phenanthrolene group, and the Ar optionally includes a substituent.

6. A composition comprising the following (a) and (b),
(a) the metal complex according to claim 1,
(b) at least one kind of component selected from a group consisting of a carbon support and a polymer.

7. A catalyst comprising:
the composition according to claim 6.

8. A catalyst comprising:
the metal complex according to claim 1.

9. An electrode catalyst for a fuel cell, comprising the catalyst according to claim 8.

* * * * *